United States Patent
Puccio et al.

(10) Patent No.: US 11,040,113 B2
(45) Date of Patent: Jun. 22, 2021

(54) METHODS AND PHARMACEUTICAL COMPOSITION FOR THE TREATMENT AND THE PREVENTION OF NEUROLOGICAL PHENOTYPE ASSOCIATED WITH FRIEDREICH ATAXIA

(71) Applicants: INSERM (INSTITUT NATIONAL DE LA SANTÉ ET DE LA RECHERCHE MÉDICALE), Paris (FR); CENTRE NATIONAL DE LA RECHERCHE SCIENTIFIQUE (CNRS), Paris (FR); UNIVERSITÉ DE STRASBOURG, Stasbourg (FR)

(72) Inventors: Hélène Puccio, Illkirch (FR); Françoise Piguet, Illkirch (FR)

(73) Assignees: INSERM (Institut National de la Santé et de la Recherche Médicale), Paris (FR); Centre National de la Recherche Scientifique (CNRS), Paris (FR); Université de Strasbourg, Strasbourg (FR)

( * ) Notice: Subject to any disclaimer, the term of this patent is extended or adjusted under 35 U.S.C. 154(b) by 51 days.

(21) Appl. No.: 15/560,620

(22) PCT Filed: Mar. 22, 2016

(86) PCT No.: PCT/EP2016/056263
§ 371 (c)(1),
(2) Date: Sep. 22, 2017

(87) PCT Pub. No.: WO2016/150964
PCT Pub. Date: Sep. 29, 2016

(65) Prior Publication Data
US 2018/0050117 A1 Feb. 22, 2018

(30) Foreign Application Priority Data
Mar. 23, 2015 (EP) .................................... 15305420

(51) Int. Cl.
*A61K 48/00* (2006.01)
*C07K 14/47* (2006.01)
*C12N 15/86* (2006.01)

(52) U.S. Cl.
CPC ............ *A61K 48/005* (2013.01); *C07K 14/47* (2013.01); *C12N 15/86* (2013.01); *C12N 2750/14143* (2013.01)

(58) Field of Classification Search
None
See application file for complete search history.

(56) References Cited

U.S. PATENT DOCUMENTS

2012/0093787 A1* 4/2012 Holmes .................. A61K 35/30
424/93.21

FOREIGN PATENT DOCUMENTS

| WO | WO-2013190059 A1 * | 12/2013 | ......... A61K 48/0075 |
| WO | 2014/118346 A1 | 8/2014 | |
| WO | WO-2015023938 A1 * | 2/2015 | ........... C12N 15/113 |

OTHER PUBLICATIONS

Gen Bank Accession No. NM_000144, *Homo sapiens* Frataxin (FXN), transcript variant 1, mRNA. Earliest Publication Date 1993. 5 Pages.*

(Continued)

*Primary Examiner* — Christopher M Babic
*Assistant Examiner* — Kimberly Aron
(74) *Attorney, Agent, or Firm* — W&C IP

(57) ABSTRACT

The present invention relates to a vector which comprises a nucleic acid sequence encoding for the frataxin (FXN) gene for use in the prevention and treatment of neurological phenotype associated with Friedreich ataxia in a subject in need thereof.

Figure 3:
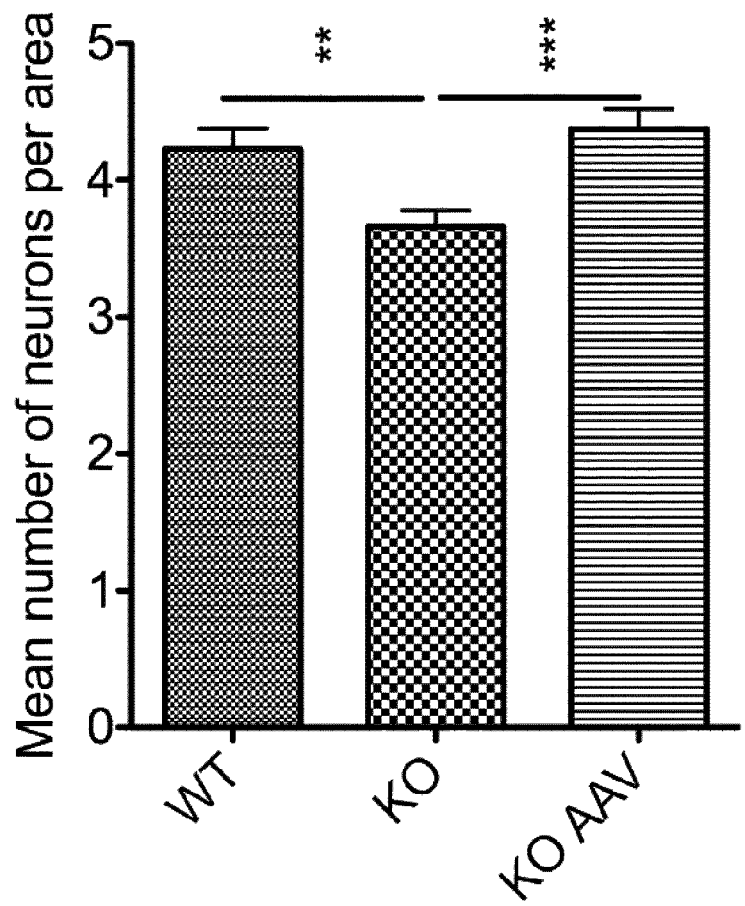

11 Claims, 7 Drawing Sheets
Specification includes a Sequence Listing.

(56) References Cited

OTHER PUBLICATIONS

Holehonnur et al. Adeno-Associated Viral Serotypes Produce Differing Titers and Differentially Transduce Neurons within the Rat Basal and Lateral Amygdala. BMC Neuroscience, 2014. 15(28): 14 pages.*

Gimenez-Cassina et al. Infectious Delivery and Long-Term Persistence of Transgene Expression in the Brain by a 135-kb iBAC-FXN Genomic DNA Expression Vector. Gene Therapy, 2001. 18:1015-1019.*

Vyas et al. A TAT-Frataxin Fusion Protein Increases Lifespan and Cardiac Function in a Conditional Friedreich's Ataxia Mouse Model. Human Molecular Genetics, 2012. 21 (6): 1230-1247.*

Claros et al. Computational Method to Predict Mitochondrially Imported Proteins and Their Targeting Sequences. Eur. J. Biochem, 1996. 241: 779-786.*

Catherine Gérard et al: "An AAV9 coding for frataxin clearly improved the symptoms and prolonged the life of friedreich ataxia mouse models", Molecular Therapy—Methods & Clinical Development, vol. 1, Jan. 1, 2014, p. 14044.

Lim Filip et al: "Functional recovery in a Friedreich's ataxia mouse model by frataxin gene transfer using an HSV-1 amplicon vector", Molecular Therapy, Nature Publishing Group, GB, vol. 15, No. 6, Jun. 1, 2007, pp. 1072-1078.

Morgane Perdomini et al: Prevention and reversal of severe mitochondrial cardiomyopathy by gene therapy in a mouse model of Friedreich's ataxia, Nature Medicine, vol. 20, No. 5, Apr. 6, 2014, pp. 542-547.

Brahim Belbellaa et al: "Vers une thérapie génique pour la cardiomyopathie associée à I ' ataxie de Friedreich", M/S Medecine Sciences., vol. 30, No. 10, Oct. 1, 2014, pp. 842-845.

J Hordeaux et al: "Efficient central nervous system AAVrh10-mediated intrathecal gene transfer in adult and neonate rats," Gene Therapy, vol. 22, No. 4, Jan. 15, 2015, pp. 316-324.

Jonathan B. Rosenberg et al: "Comparative Efficacy and Safety of Multiple Routes of Direct CNS Administration of Adeno-Associated Virus Gene Transfer Vector Serotype rh. 10 Expressing the Human Arylsulfatase A cDNA to Nonhuman Primates", Human Gene Therapy Clinical Development, vol. 25, No. 3, Sep. 1, 2014, pp. 164-177.

* cited by examiner

A
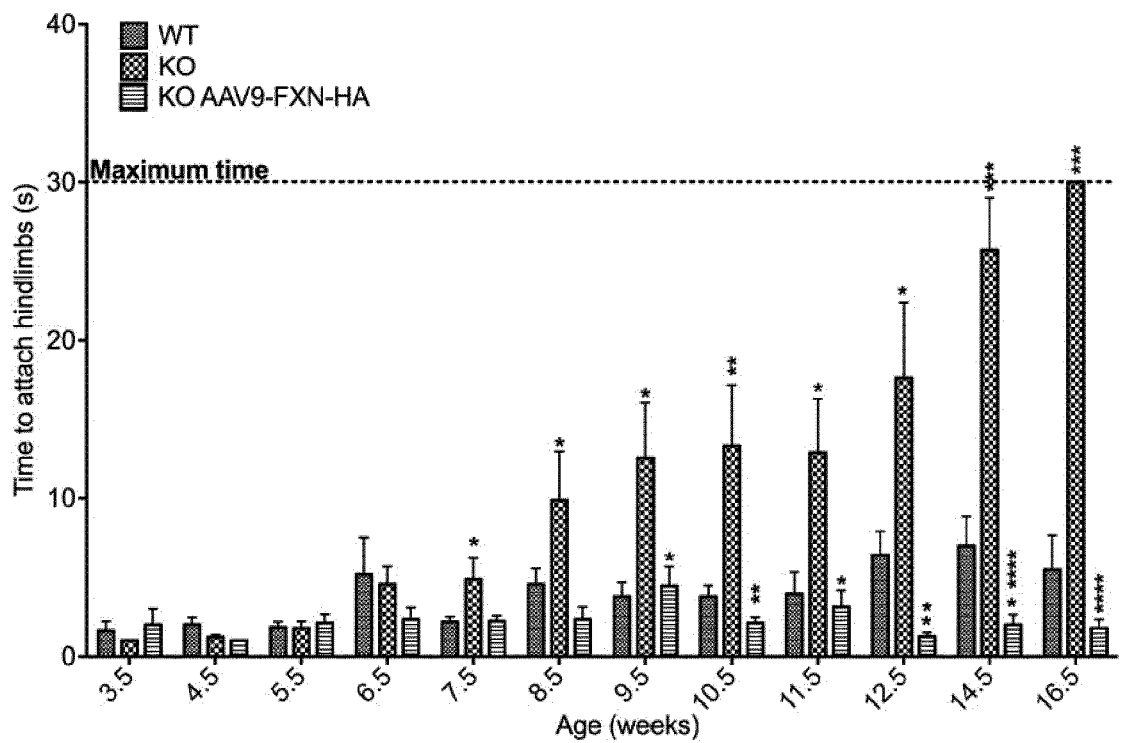
B
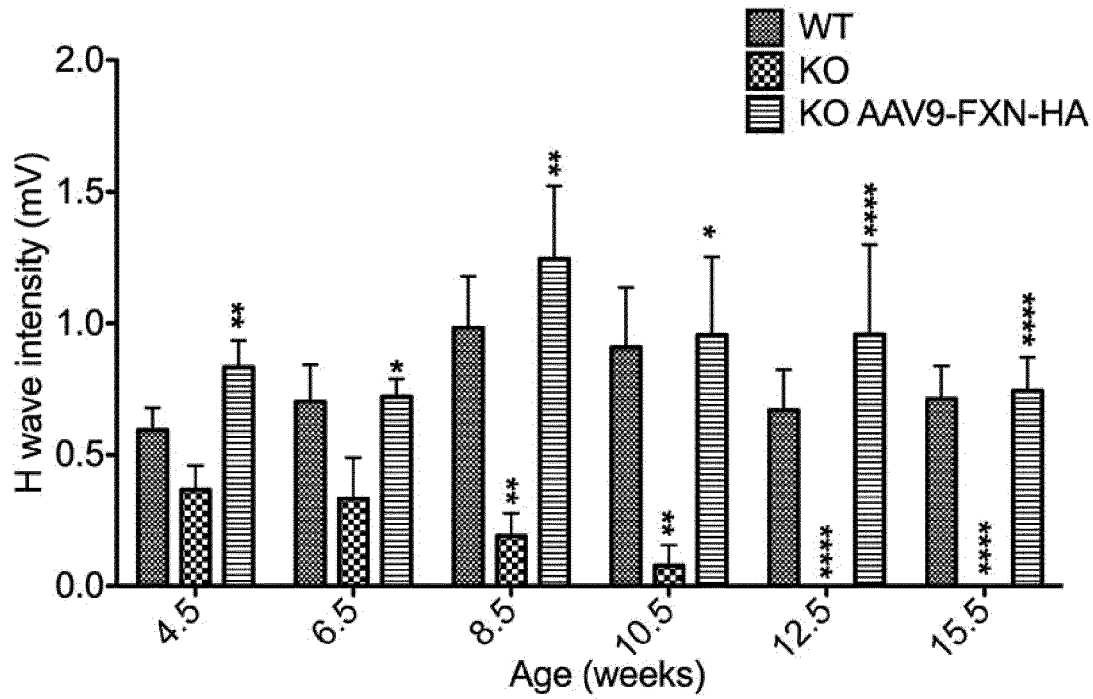
Figure 1 A and B

A
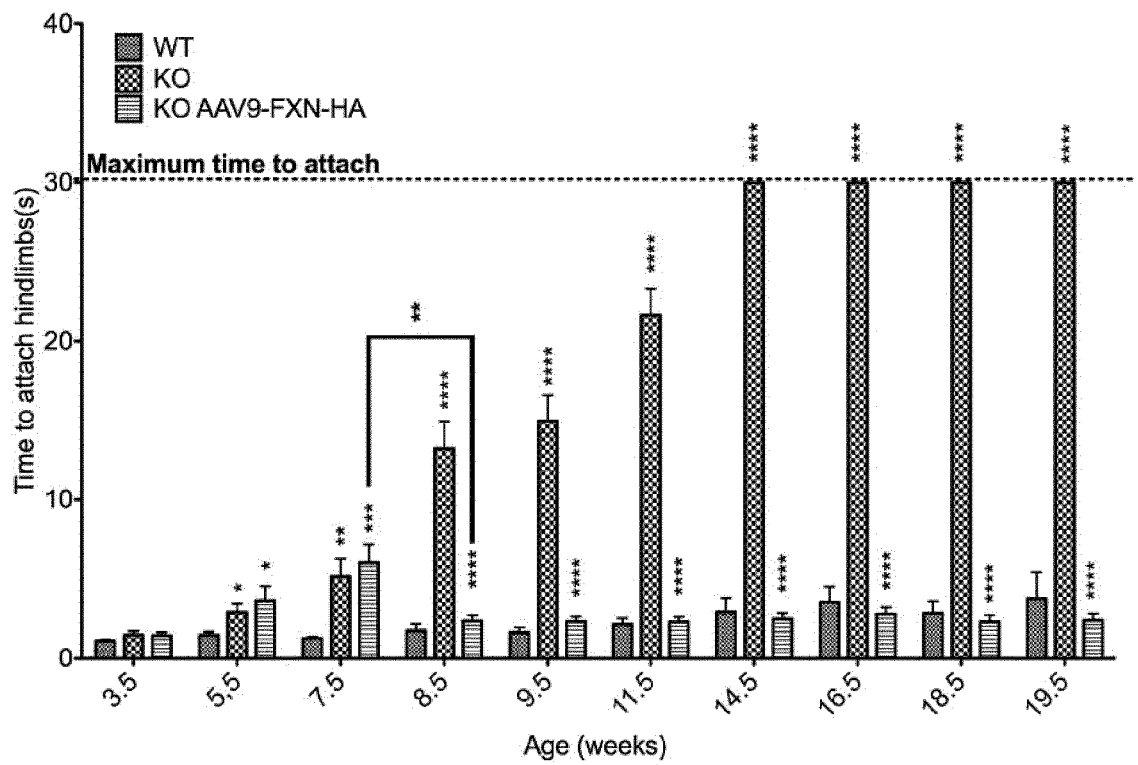
B
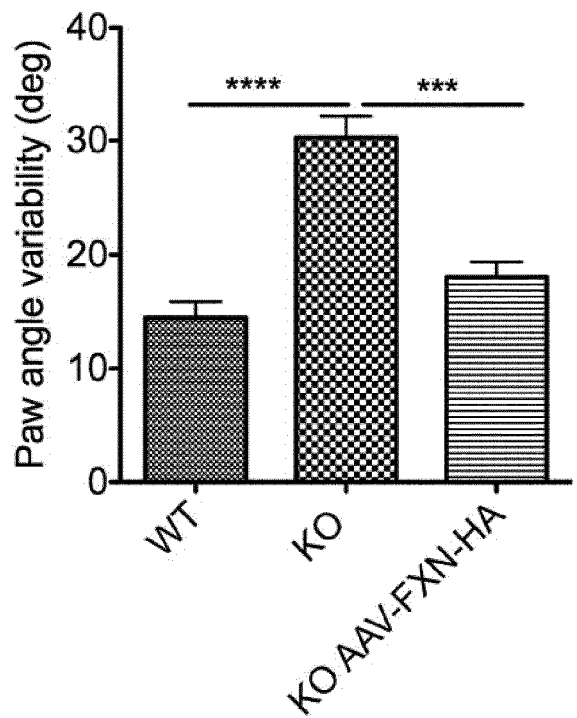
Figure 2 A and B

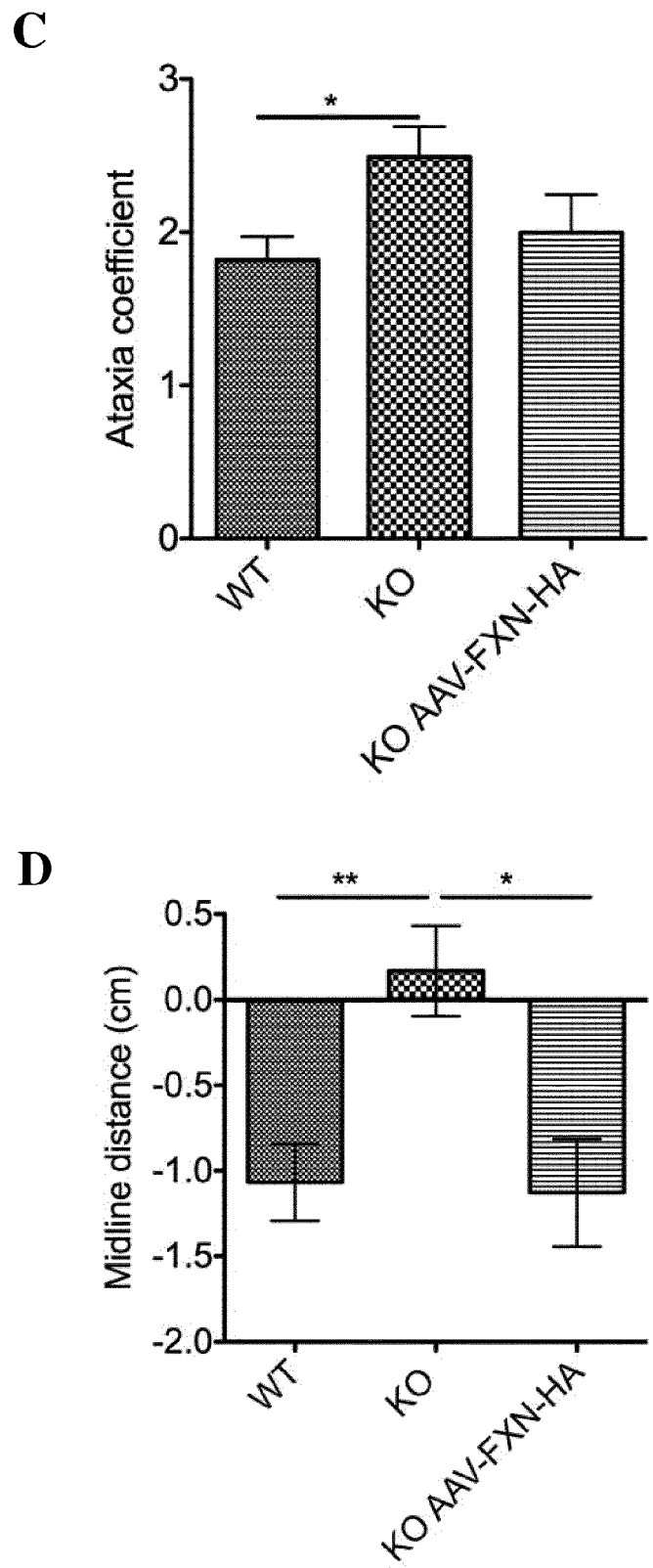
Figure 2 C and D

METHODS AND PHARMACEUTICAL COMPOSITION FOR THE TREATMENT AND THE PREVENTION OF NEUROLOGICAL PHENOTYPE ASSOCIATED WITH FRIEDREICH ATAXIA

FIELD OF THE INVENTION

The present invention relates to a vector which comprises a nucleic acid sequence encoding for the frataxin (FXN) gene for use in the prevention and treatment of neurological phenotype associated with Friedreich ataxia in a subject in need thereof.

BACKGROUND OF THE INVENTION

Friedreich's ataxia (FRDA) (Harding et al 1981 and Koeppen et al 2013), the most common form of inherited ataxia with an incidence in 1/50,000 in the Caucasian population, is characterized by progressive limb and gait ataxia, absent of lower limb reflexes, extensor plantar responses, dysarthria, cardiomyopathy and an increased incidence of diabetes mellitus. Onset of the symptoms is typically in adolescence and usually before 25 years of age. Cardiac dysfunction leading to congestive heart failure and arrhythmias is the cause of death in 59% of FRDA patients.

The main sites of pathology include the central and peripheral nervous system and cardiac muscle. The first pathological changes occur in the dorsal root ganglia (DRG) with two major features: the loss of large sensory neurons and appearance of residual nodules deriving of satellite or Schwann cells. Dorsal spinal roots are thinner and characterized by a lack of large axons as well as thick myelinated fibers. This is followed by neuronal degeneration in Clarke's columns due to transneuronal ascending degeneration of dorsal spinocerebellar tract. More severe degeneration is observed in gracile and cuneate fasciculi most probably due to anterograde connection and thus degeneration. In accordance with large neurons of the DRG, FRDA patients develop a sensory peripheral neuropathy, which is more severe in lower limbs. Biopsies reveal a persistence of thin axons and a lack of large myelinated fibers and decrease number of S100-positive Schwann cells. A main hypothesis is that in young patients begins a lack of myelination and myelin repair, which is worsening overtime because of axonal disease. In the CNS, main affections are located in the Dentate Nucleus (DN) and characterized by an atrophy of the DN and its efferent myelinated fibers with specific loss of neurons. DN crosstalk with contralateral inferior olivary nucleus, that remains intact in patients. Two third of afferences of the DN come from Purkinje cells but no retrograde atrophy is observed in patients. Even if still controversial, a hypothesis is that DN is still intact in childhood and adolescence. FRDA patients display similarities in their corticospinal tracts with upper motor neuron lesions of ALS patients which suggests a possible "dying back" neuropathy (Koeppen, 2013). Cardiomyopathy and diabetes reflect independent site of primary degeneration.

FRDA is caused by mutations in the FXN gene on 9q21, which encodes a small mitochondrial protein called frataxin. Most FRDA patients (96%) are homozygous for a GAA trinucleotide expansion within the first intron, which causes transcriptional silencing through a mechanism involving epigenetic changes, leading ultimately to a drastic reduction in the levels of the frataxin mRNA as compared to normal individuals. Patients thus show a strong reduction of the frataxin protein in all tissues. Indeed, FRDA patients show significant lower amounts of frataxin protein compared to control, with 21.1% in buccal cells and 32.2% in whole blood (Deutsch, Santani et al. 2010). A subset of patients (4%) is compound heterozygous for a GAA expansion and a more classical mutation (point mutation, small deletion or insertion) on the other allele leading to loss of function of the frataxin protein. While the total absence of frataxin in model organism is associated with embryonic lethality, both the age of onset and the severity of the disease inversely correlate to the expansion size of the GAA repeat.

The FXN gene is composed of seven exons spread over 85 kb of genomic DNA. The major transcript (1.3 kb) synthesized from the FXN gene is composed of the first five exons, localized within a 40 kb interval. Alternative transcripts have been reported, but their physiological relevance is uncertain. The major transcript encodes a 210-amino acid protein which undergoes a maturation process, as most nuclear-encoded mitochondrial proteins (Koutnikova, Campuzano et al. 1998 and Cavadini, Adamec et al. 2000). The targeting sequence of frataxin is contained between amino acids 1-80, consisting of positively charge residues (Arginines) in an alpha-helix. However, its maturation process is unusual as it occurs in two steps by the mitochondrial processing peptidase (Koutnikova, Campuzano et al. 1998 and Cavadini, Adamec et al. 2000). The two steps are a cleavage between positions 41 and 42 leading to the intermediate form of frataxin, followed by cleavage that results in the mature form starting at amino acid 81 (Condo, Ventura et al. 2007 and Schmucker, Argentini et al. 2008).

The FXN gene is ubiquitously expressed although at variable levels in different tissues and during development. Differences in mitochondrial mass cannot fully account for differences in FXN expression. Overall, FXN expression is high in the primary sites of degeneration in FRDA, both within and outside the CNS. It has been proposed that somatic instability of the GAA expansion might account in part for the selective vulnerability of specific neurons and disease progression. Reduced levels of frataxin result in mitochondrial dysfunction, in particular with the loss of Fe—S cluster enzyme activities (aconitase and respiratory chain complexes I-III), mitochondrial iron accumulation and increase sensitivity to oxidative stress. Frataxin is a highly evolutionary conserved protein which exact physiological function is still a matter of debate. Although frataxin has been proposed to be a multifunctional protein involved in different iron-dependent mitochondrial pathways, phylogenetic, genetic and biochemical studies point to the essential role of frataxin in Fe—S cluster metabolism (Huynen, Snel et al. 2001; Muhlenhoff, Richhardt et al. 2002; Adinolfi, Iannuzzi et al. 2009; Tsai and Barondeau 2010 and Schmucker, Martelli et al. 2011). Recent experiments demonstrate that frataxin stabilizes the complex composed of ISD11, ISCU, NFS1 that is responsible for de novo Fe—S cluster biogenesis, and controls iron entry through activation of the cysteine desulfurase activity thereby acting as a regulator of Fe—S cluster biogenesis (Colin et al 2013). Fe—S clusters are integral parts of proteins involved in numerous essential physiological processes ranging from nuclear genome synthesis and stability, protein translation to mitochondrial metabolism and respiration. The absence or decrease of frataxin is associated with severe loss of activity in Fe—S containing proteins, such as aconitase, and loss of energy production.

SUMMARY OF THE INVENTION

By working on different model of Friedreich ataxia, the inventors show that use of AAV which comprise the frataxin (FXN) encoding nucleic acid correct the early-symptomatic neurological phenotype of mice, completely preventing the onset of the sensori-motor defect and degeneration of the dorsal root ganglia. Furthermore, the inventors show that combined intravenous and intracerebral administration of AAV9 and AAVrh.10, respectively, which both comprise the frataxin (FXN) encoding nucleic acid, correct the post-symptomatic neurological phenotype of mice, in particular the sensori-motor defect and degeneration of the dorsal root ganglia and the cerebellar dysfunction/degeneration. Thus, use of AAV which comprise the frataxin (FXN) encoding nucleic acid will be benefit for treatment and prevention of neurological phenotype in patient with Friedreich ataxia.

Thus, the invention relates to a vector which comprises a nucleic acid sequence encoding for the frataxin (FXN) gene for use in the prevention and treatment of neurological phenotype associated with Friedreich ataxia in a subject in need thereof.

DETAILED DESCRIPTION OF THE INVENTION

Methods of the Invention

A first object of the invention relates to a vector which comprises a nucleic acid sequence encoding for the frataxin (FXN) gene for use in the prevention and treatment of neurological phenotype associated with Friedreich ataxia in a subject in need thereof.

As used herein in its broadest meaning, the term "prevention" or "preventing" refers to preventing the disease or condition from occurring in a subject which has not yet been diagnosed as having it or which does not have any clinical symptoms.

As used herein, the term "treatment" or "treating" as used herein, means reversing, alleviating, stabilisation or inhibiting the progress of the disorder or condition to which such term applies, or one or more symptoms of such disorder or condition. A "therapeutically effective amount" is intended for a minimal amount of active agent which is necessary to impart therapeutic benefit to a subject. For example, a "therapeutically effective amount" to a patient is such an amount which induces, ameliorates, stabilises, slows down the progression or otherwise causes an improvement in the pathological symptoms, disease progression or physiological conditions associated with or resistance to succumbing to a disorder.

As used herein, the term "subject" denotes a mammal, such as a rodent, a feline, a canine, and a primate. Preferably a subject according to the invention is a human. In the context of the present invention, a "subject in need thereof" denotes a subject, preferably a human, with neurological phenotype associated with Friedreich ataxia. Subject with neurological phenotype associated with Friedreich ataxia presents some symptoms which may be, but are not limited to, mixed spinocerebellar and sensory ataxia, dysarthria, vision and hearing loss, dysphagia, areflexia. Thus, the method of the invention will be very useful to treat subject with such disease (Friedreich ataxia) presenting such symptoms.

As used herein, the term "gene" refers to a polynucleotide containing at least one open reading frame that is capable of encoding a particular polypeptide or protein after being transcribed and translated.

As used herein, the terms "coding sequence", "a sequence which encodes a particular protein" or "nucleic acid sequence encoding", denotes a nucleic acid sequence which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, cDNA from prokaryotic or eukaryotic mRNA, genomic DNA sequences from prokaryotic or eukaryotic DNA, and even synthetic DNA sequences.

As used herein, the term "neurological phenotype associated with Friedreich ataxia" denotes neurological features or disorders like loss of joint position and vibration sense in the limbs typical features of ataxia (which mostly results from degeneration of the dorsal root ganglia neurons, spinocerebellar tract, the cerebellar dentate nucleus), dysarthria (dentate nucleus involvement), vision with saccadic pursuit (optic nerve atrophy and dentate nucleus involvement) and hearing loss (central nerve involvement suggested by abnormal brainstem evoked auditory potentials), dysphagia (dentate nucleus involvement), areflexia (degeneration of peripheral nerves resulting of neuronal loss within DRG) and pyramidal syndrome and weakness identified with Babinski sign (dying back in cortico-spinal tracts).

According to the invention, the term "neurological phenotype associated with Friedreich ataxia" can be replace by "neurological disorders associated with Friedreich ataxia" or "neurological features associated with Friedreich ataxia" with the same meaning.

Thus, in a particular embodiment, the invention relates to a vector which comprises a nucleic acid sequence encoding for the frataxin (FXN) gene for use in the prevention and treatment of ataxia and/or dysarthria associated with Friedreich ataxia in a subject in need thereof.

In a particular embodiment, the invention also relates to a vector which comprises a nucleic acid sequence encoding for the frataxin (FXN) gene for use in the reversion of neurological phenotype associated with Friedreich ataxia in a subject in need thereof.

In a particular embodiment, the invention also relates to a vector which comprises a nucleic acid sequence encoding for the frataxin (FXN) gene for use in the stabilisation of neurological phenotype associated with Friedreich ataxia in a subject in need thereof.

In a particular embodiment, the invention also relates to a vector which comprises a nucleic acid sequence encoding for the frataxin (FXN) gene for use in the restoration of neurological functions in a subject with neurological phenotype associated with Friedreich ataxia in a subject in need thereof.

As used herein, the term "reversion of neurological phenotype associated with Friedreich ataxia" or "restoration of neurological functions in a subject with neurological phenotype associated with Friedreich ataxia" denotes the restoration or correction of neurological function by, for example, reversing the sensory or spinocereberebellar ataxia, the dysarthria, the hearing or vision loss or restoring reflexes.

As used herein, the term "stabilisation of neurological phenotype associated with Friedreich ataxia" denotes the slowing or halting development of neurological problems as described above.

In another particular embodiment, the invention also relates to a vector which comprises a nucleic acid sequence encoding for the frataxin (FXN) gene for use in the prevention or treatment of neurological phenotype associated with Friedreich ataxia in an asymptomatic, pre-symptomatic or early-symptomatic subject in need thereof.

In another particular embodiment, the invention also relates to a vector which comprises a nucleic acid sequence encoding for the frataxin (FXN) gene for use in the prevention or treatment of neurological phenotype associated with Friedreich ataxia in an symptomatic, post-symptomatic or late-symptomatic subject in need thereof.

As used herein, the terms "asymptomatic", "pre-symptomatic" or "early-symptomatic" denotes a subject with the disease (Friedreich ataxia) as defined by a genetic diagnosis (see for review Lynch D R et al., 2002) but with no overt clinical neurological symptom.

As used herein, the terms "symptomatic", "post-symptomatic" or "late-symptomatic" denotes a subject with the disease (Friedreich ataxia) as defined by a genetic diagnosis and with the presence of neurological symptoms (sensory and spinocerebellar ataxia, dysarthria, vision and hearing loss, dysphagia, areflexia, loss of joint position and vibration sense in the lower limbs).

The FXN gene encodes the protein frataxin. This frataxin is a protein localized to the mitochondrion. The frataxin is involved in assembly of iron-sulfur clusters by regulating iron entry and the activity of the cysteine desulfurase. A cDNA sequence for human FXN (transcript variant 1) is disclosed in Genbank Access Number NM_000144 or NG_008845 (SEQ ID NO:1). The amino acid sequence of human frataxin is shown in SEQ ID NO:2.

The sequence of the nucleic acid of the frataxin (cDNA) is (SEQ ID NO: 1):

```
agtctccctt gggtcagggg tcctggttgc actccgtgct
ttgcacaaag caggctctcc attttgtta aatgcacgaa
tagtgctaag ctgggaagtt cttcctgagg tctaacctct
agctgctccc ccacagaaga gtgcctgcgg ccagtggcca
ccaggggtcg ccgcagcacc cagcgctgga gggcggagcg
ggcggcagac ccggagcagc atgtggactc tcgggcgccg
cgcagtagcc ggcctcctgg cgtcacccag cccagcccag
gcccagaccc tcacccgggt cccgcggccg gcagagttgg
ccccactctg cggccgccgt ggcctgcgca ccgacatcga
tgcgacctgc acgccccgcc gcgcaagttc gaaccaacgt
ggcctcaacc agatttggaa tgtcaaaaag cagagtgtct
atttgatgaa tttgaggaaa tctggaactt tgggccaccc
aggctctcta gatgagacca cctatgaaag actagcagag
gaaacgctgg actctttagc agagttttt gaagaccttg
cagacaagcc atacacgttt gaggactatg atgtctcctt
tgggagtggt gtcttaactg tcaaactggg tggagatcta
ggaacctatg tgatcaacaa gcagacgcca aacaagcaaa
tctggctatc ttctccatcc agtggaccta agcgttatga
ctggactggg aaaaactggg tgtactccca cgacggcgtg
tccctccatg agctgctggc cgcagagctc actaaagcct
taaaaaccaa actggacttg tcttccttgg cctattccgg
```

-continued
```
aaaagatgct tgatgcccag ccccgtttta aggacattaa
aagctatcag gccaagaccc cagcttcatt atgcagctga
ggtctgtttt ttgttgttgt tgttgtttat ttttttttatt
cctgcttttg aggacagttg ggctatgtgt cacagctctg
tagaaagaat gtgttgcctc ctaccttgcc cccaagttct
gatttttaat ttctatggaa gattttttgg attgtcggat
ttcctccctc acatgatacc ccttatcttt tataatgtct
tatgcctata cctgaatata caaccttta aaaaagcaaa
ataataagaa ggaaaaattc caggagggaa aatgaattgt
cttcactctt cattctttga aggatttact gcaagaagta
catgaagagc agctggtcaa cctgctcact gttctatctc
caaatgagac acattaaagg gtagcctaca aatgttttca
ggcttcttt aaagtgtaag cacttctgag ctctttagca
ttgaagtgtc gaaagcaact cacacgggaa gatcatttct
tatttgtgct ctgtgactgc caaggtgtgg cctgcactgg
gttgtccagg gagacctagt gctgtttctc ccacatattc
acatacgtgt ctgtgtgtat atatattttt tcaatttaaa
ggttagtatg gaatcagctg ctacaagaat gcaaaaaat
ttccaaagac aagaaaagag gaaaaaaagc cgttttcatg
agctgagtga tgtagcgtaa caaacaaaat catggagctg
aggaggtgcc ttgtaaacat gaaggggcag ataaaggaag
gagatactca tgttgataaa gagagccctg gtcctagaca
tagttcagcc acaaagtagt tgtcccttg tggacaagtt
tcccaaattc cctggacctc tgcttcccca tctgttaaat
gagagaatag agtatggttg attcccagca ttcagtggtc
ctgtcaagca acctaacag ctagttctaa ttccctattg
ggtagatgag gggatgacaa agaacagttt ttaagctata
taggaaacat tgttattggt gttgccctat cgtgatttca
gttgaattca tgtgaaaata atagccatcc ttggcctggc
gcggtggctc acacctgtaa tcccagcact tttggaggcc
aaggtgggtg gatcacctga ggtcaggagt tcaagaccag
cctggccaac atgatgaaa cccgtctcta ctaaaaatac
aaaaaattag ccgggcatga tggcaggtgc ctgtaatccc
agctacttgg gaggctgaag cggaagaatc gcttgaaccc
agaggtggag gttgcagtga gccgagatcg tgccattgca
ctgtaacctg ggtgactgag caaactctg tctcaaaata
ataataacaa tataataata ataatagcca tcctttattg
taccttact gggttaatcg tattatacca cattacctca
ttttaatttt tactgacctg cactttatac aaagcaacaa
gcctccagga cattaaaatt catgcaaagt tatgctcatg
ttatattatt ttcttactta aagaaggatt tattagtggc
```

```
tgggcatggt ggcgtgcacc tgtaatccca ggtactcagg
aggctgagac gggagaattg cttgacccca ggcggaggag
gttacagtga gtcgagatcg tacctgagcg acagagcgag
actccgtctc aaaaaaaaaa aaaaggaggg tttattaatg
agaagtttgt attaatatgt agcaaaggct tttccaatgg
gtgaataaaa acacattcca ttaagtcaag ctgggagcag
tggcatatac ctatagtccc agctgcacag gaggctgaga
caggaggatt gcttgaagcc aggaattgga gatcagcctg
ggcaacacag caagatccta tctcttaaaa aagaaaaaa
aaacctatta ataataaaac agtataaaca aaagctaaat
aggtaaaata ttttttctga aataaaatta ttttttgagt
ctgatggaaa tgtttaagtg cagtaggcca gtgccagtga
gaaaataaat aacatcatac atgtttgtat gtgtttgcat
cttgcttcta ctgaaagttt cagtgcaccc cacttactta
gaactcggtg acatgatgta ctcctttatc tgggacacag
cacaaaagag gtatgcagtg gggctgctct gacatgaaag
tggaagttaa ggaatctggg ctcttatggg gtccttgtgg
gccagcccct caggcctatt ttactttcat tttacatata
gctctaattg gtttgattat ctcgttccca aggcagtggg
agatccccat ttaaggaaag aaaaggggcc tggcacagtg
gctcatgcct gtaatcccag cactttggga ggctgaggca
agtgtatcac ctgaggtcag gagttcaaga ccagcctggc
caacatggca aaatcccgtc tctactaaaa atattaaaaa
attggctggg cgtggtggtt cgtgcctata atttcagcta
ctcaggaggc tgaggcagga gaatcgctgt aacctggggg
gtggaggttg cagtgagacg agatcatgcc acttcactcc
agcctggcca acagagcca actccgtctc aaataaataa
ataaataaat aaagggactt caaacacatg aacagcagcc
aggggaagaa tcaaaatcat attctgtcaa gcaaactgga
aaagtaccac tgtgtgtacc aatagcctcc ccaccacaga
ccctgggagc atcgcctcat ttatggtgtg gtccagtcat
ccatgtgaag gatgagtttc caggaaaagg ttattaaata
ttcactgtaa catactggag gaggtgagga attgcataat
acaatcttag aaaacttttt tttccccttt ctatttttg
agacaggatc tcactttggc actcaggctg gaggacagtg
gtacaatcaa agctcatggc agcctcgacc tccctgggct
tgggcaatcc tcccacaggt gtgcacctcc atagctggct
aatttgtgta ttttttgtag agatggggtt tcaccatgtt
gcccaggctg gtctctaaca cttaggctca agtgatccac
ctgcctcgtc ctcccaagat gctgggatta caggtgtgtg
ccacaggtgt tcatcagaaa gcttttttcta ttattttac
cttcttgagt gggtagaacc tcagccacat agaaaataaa
atgttctggc atgacttatt tagctctctg gaattacaaa
gaaggaatga ggtgtgtaaa agagaacctg ggttttgaa
tcacaaattt agaatttaat cgaaactctg cctcttactt
gtttgtagac actgacagtg gcctcatgtt ttttttttt
ttaatctata aaatggagat atctaacatg ttgagcctgg
gcccacaggc aaagcacaat cctgatgtga gaagtactca
gttcatgaca actgttgttc tcacatgcat agcataattt
catattcaca ttggaggact tctcccaaaa tatggatgac
gttccctact caaccttgaa cttaatcaaa atactcagtt
tacttaactt cgtattagat tctgattccc tggaaccatt
tatcgtgtgc cttaccatgc ttatatttta cttgatcttt
tgcatacctt ctaaaactat tttagccaat ttaaaatttg
acagtttgca ttaaattata ggtttacaat atgctttatc
cagctatacc tgccccaaat tctgacagat gcttttgcca
cctctaaagg aagacccatg ttcatagtga tggagtttgt
gtggactaac catgcaaggt tgccaaggaa aaatcgcttt
acgcttccaa ggtacacact aagatgaaag taattttagt
ccgtgtccag ttggattctt ggcacatagt tatcttctgc
tagaacaaac taaaacagct acatgccagc aagggagaaa
gggaaggag gggcaaagtt tgaaatttc atgtaaattt
atgctgttca aaacgacgag ttcatgactt tgtgtataga
gtaagaaatg ccttttcttt tttgagacag agtcttgctc
tgtcacccag gctggagtgc agtggcacga tctgggctca
ctacaacctc cgcctcctgg gttcaagcaa ttctctgcct
cagcctcccg agtagctggg attacaggtg cctgccacca
cacccggcta ttttttgtat tttagtaga cggggttt
caccatcatg gccaggctgg tcttgaactc ctgacctagt
aatccacctg cctccgcctc ccaaagtgct gggattacag
gcgtgagcca ctgcacccag ccagaaatgc cttctaatct
ttggtttatc ttaattagcc aggacacttg gagtgcatcc
cgaagtacct gatcagtggc ccctttggaa tgtgtaaaac
tcagctcact tatatccctg catccgctac agagacagaa
tccaagctca tatgttccat cttctctggc tgtatagttt
aaggaatgga aggcaccaga acagatttat tgaaatgttt
attagctgaa gatttattta gacagttgag gaaaacatca
gcacccagca gtaaaattgg ctctcaaaga ttttcttctc
ctgtggaaag tcagacctct gaggccccat ccaggtagaa
```

```
gtactagtgc aagaagggcc tctgctgtcc acttgtgttt ctgtgatctg tgggaacatt gttaacgcca catcttgacc tcaaattgtt tagctcctgg ccagacacgg tggctcacac ctgtaatccc agcactttga gaggctgagg caggtggatc acctgaggtt aggagttcga ggccagcctg gtcaacatgg taaaacccg cctctactaa aaatacaaaa attagctggc cgtagtggcg cacgcctgtt atcccagcta ctcgggaggc tgaggcagga gaattgcttg aacctgggtg gtggaggttg cagtgagccg agattacacc actgcactcc agcctgggtg acaagaggga aactccatta aaaaaatgta attcccgtgt ctgccatctt aagtgtaaag gtggctaaat tatatagaaa aataagacaa tatcatttcc caattacatt cctttcctac cgcactctat gatgctagct gagattttc caaaagaaaa tggcttaaat aaaaccta gagaaagaaa aactttaaat ccctccaaag ctcaaaagta atagaaacag atgagtttgg agtcaggatt tctctgtaag attgcctagg ctgtgtactg cacatctcca ggtgccactg ttgacagaga ttataactac aatgtgaagt gaatggtgcc actgacagtt atgcaaaccg tccagagcat agccacctga tcctgctggg attcctcttg ccagtccatc agcagttccc cttgaaagtt tcaccaaaca tcccttaaat ctgccctctc ctgcccgtcc ccagtggagg tcctcatcat tttcacctg cattttgca ggagctttct tatatccacc ttcctccttt tctctcagcc catcatctag ctacacagtc tccagggtaa gctttcagaa aggcaatctc ttgtctgtaa aacctaagca ggaccaaggc caagtttctt agcctgaaaa atgtgctttt ctgactgaac tgttcaggca ctgactctac atataattat gcttttctac cccctcacac tcaacacttt gactccagca atcccaaatc cccagatccc taagtgtgct gtgctatttt cacgtggctc tcagacttgg ccagtgctgt ttccatttg gtctttattc cccacatctc tgcctggggg gtagattcta ccctgaaaaa tgttcttggc acagccttgc aaactcctcc tccactcagc ctctgcctgg atgcccttga ttgttccatg tcctcagcat accatgtttg tctttcccag cactgaccta ccatgtgtca ccctgcttg gctgtaccctt ccatgaggct aggactatgt gtctcctttg ttgactgctg ttgccctagc atcttgcaca gttccttgca cacaattaga gctctataaa tgtcaaataa atgtgttata attatatgtt taagatagtt gttcaaataa actctaaata accccaac.
```

The sequence of the frataxin protein is (SEQ ID NO:2):

MWTLGRRAVAGLLASPSPAQAQTLTRVPRPAELAPLCGRRGLRTDID

ATCTPRRASSNQRGLNQIWNVKKQSVYLMNLRKSGTLGHPGSLDETT

YERLAEETLDSLAEFFEDLADKPYTFEDYDVSFGSGVLTVKLGGDLG

TYVINKQTPNKQIWLSSPSSGPKRYDWTGKNWVYSHDGVSLHELLAA

ELTKALKTKLDLSSLAYSGKDA.

In a particular embodiment, the invention provides a nucleic acid construct comprising sequence SEQ ID NO:1 or a variant thereof for treating or preventing neurological phenotype associated with Friedreich ataxia.

The variants include, for instance, naturally-occurring variants due to allelic variations between individuals (e.g., polymorphisms), alternative splicing forms, in particular transcript variants 2 and 3 (accession numbers NM_001161706 and NM_181425), etc. The term variant also includes FXN gene sequences from other sources or organisms. Variants are preferably substantially homologous to SEQ ID NO:1, i.e., exhibit a nucleotide sequence identity of typically at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% with SEQ ID NO: 1. Variants of a FXN gene also include nucleic acid sequences, which hybridize to a sequence as defined above (or a complementary strand thereof) under stringent hybridization conditions. Typical stringent hybridisation conditions include temperatures above 30° C., preferably above 35° C., more preferably in excess of 42° C., and/or salinity of less than about 500 mM, preferably less than 200 mM. Hybridization conditions may be adjusted by the skilled person by modifying the temperature, salinity and/or the concentration of other reagents such as SDS, SSC, etc.

In a particular embodiment, the FXN-encoding nucleic acid is a fragment of the SEQ ID NO:1 which encodes for the amino acid sequence 81-210 of the SEQ ID NO:2 (named variant "81-210") or a variant thereof, "variant" having the meaning provided above with respect to nucleotide sequence identity and hybridization.

In a another particular embodiment, a sequence known as mitochondrion-targeting signal or mitochondrial targeting signal may be added to the FXN-encoding sequence or variant thereof, including, for example the FXN-encoding sequence "81-210". Sequences known as mitochondrion-targeting signal or mitochondrial targeting signal are referred to as MTS by the skilled person.

A MTS sequence can be identified within a protein or nucleic acid sequence by a person of ordinary skill in the art.

Most mitochondrion-targeting peptides consist of a N-terminal pre-sequence of about 15 to 100 residues, preferably of about 20 to 80 residues. They are enriched in arginine, leucine, serine and alanine. Mitochondrial pre-sequences show a statistical bias of positively charged amino acid residues, provided mostly through arginine residues; very few sequences contain negatively charged amino acids. Mitochondrion-targeting peptides also share an ability to form an amphiphilic alpha-helix.

A complete description of a method to identify a MTS is available in: M. G. Claros, P. Vincens, 1996 (Eur. J. Biochem. 241, 779-786 (1996), "Computational method to predict mitochondrially imported proteins and their targeting sequences"), the content of which is herein incorporated by reference.

In a particular embodiment, the invention also relates to a method for preventing and treating the neurological phenotype associated with Friedreich ataxia in a subject in need thereof, comprising administering to said subject a therapeutically effective amount of a vector which comprises a frataxin (FXN) encoding nucleic acid.

In a particular embodiment, the invention relates to a method for reversing or stabilising the neurological phenotype associated with Friedreich ataxia in a subject in need thereof, comprising administering to said subject a therapeutically effective amount of a vector which comprises a frataxin (FXN) encoding nucleic acid.

In another particular embodiment, the invention relates to a method for restoring neurological functions in a subject suffering of neurological phenotype associated with Friedreich ataxia comprising administering to said subject of a therapeutically effective amount of a vector which comprises a frataxin (FXN) encoding nucleic acid.

Non Viral Vectors

In a particular embodiment, the vector use according to the invention is a non viral vector. Typically, the non viral vector may be a plasmid which includes nucleic acid sequences encoding FXN gene, or variants thereof, as described above.

The Viral Vectors

Gene delivery viral vectors useful in the practice of the present invention can be constructed utilizing methodologies well known in the art of molecular biology. Typically, viral vectors carrying transgenes are assembled from polynucleotides encoding the transgene, suitable regulatory elements and elements necessary for production of viral proteins which mediate cell transduction.

The terms "Gene transfer" or "gene delivery" refer to methods or systems for reliably inserting foreign DNA into host cells. Such methods can result in transient expression of non integrated transferred DNA, extrachromosomal replication and expression of transferred replicons (e.g. episomes), or integration of transferred genetic material into the genomic DNA of host cells.

Examples of viral vector include but are not limited to adenoviral, retroviral, lentiviral, herpesvirus and adeno-associated virus (AAV) vectors.

Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO95/14785, WO96/22378, U.S. Pat. Nos. 5,882,877, 6,013,516, 4,861, 719, 5,278,056 and WO94/19478.

In one embodiment, adeno-associated viral (AAV) vectors are employed.

In other embodiments, the AAV vector is AAV1, AAV2, AAV3, AAV4, AA5, AAV6, AAV7, AAV8, AAV9, AAVrh.10 or any other serotypes of AAV that can infect humans, monkeys or other species.

In one particular embodiment, the AAV vector is an AAV9 or AAVrh.10.

By an "AAV vector" is meant a vector derived from an adeno-associated virus serotype, including without limitation, AAV-1, AAV-2, AAV-3, AAV-4, AAV-5, AAV6, etc. AAV vectors can have one or more of the AAV wild-type genes deleted in whole or part, preferably the rep and/or cap genes, but retain functional flanking ITR sequences. Functional ITR sequences are necessary for the rescue, replication and packaging of the AAV virion. Thus, an AAV vector is defined herein to include at least those sequences required in cis for replication and packaging (e.g., functional ITRs) of the virus. The ITRs need not be the wild-type nucleotide sequences, and may be altered, e.g. by the insertion, deletion or substitution of nucleotides, so long as the sequences provide for functional rescue, replication and packaging. AAV expression vectors are constructed using known techniques to at least provide as operatively linked components in the direction of transcription, control elements including a transcriptional initiation region, the DNA of interest (i.e. the FXN gene) and a transcriptional termination region.

The control elements are selected to be functional in a mammalian cell. The resulting construct which contains the operatively linked components is bounded (5' and 3') with functional AAV ITR sequences. By "adeno-associated virus inverted terminal repeats" or "AAV ITRs" is meant the art-recognized regions found at each end of the AAV genome which function together in cis as origins of DNA replication and as packaging signals for the virus. AAV ITRs, together with the AAV rep coding region, provide for the efficient excision and rescue from, and integration of a nucleotide sequence interposed between two flanking ITRs into a mammalian cell genome. The nucleotide sequences of AAV ITR regions are known. See, e.g., Kotin, 1994; Berns, K I "Parvoviridae and their Replication" in Fundamental Virology, 2nd Edition, (B. N. Fields and D. M. Knipe, eds.) for the AAV-2 sequence. As used herein, an "AAV ITR" does not necessarily comprise the wild-type nucleotide sequence, but may be altered, e.g., by the insertion, deletion or substitution of nucleotides. Additionally, the AAV ITR may be derived from any of several AAV serotypes, including without limitation, AAV-1, AAV-2, AAV-3, AAV-4, AAV-5, AAV-6, etc. Furthermore, 5' and 3' ITRs which flank a selected nucleotide sequence in an AAV vector need not necessarily be identical or derived from the same AAV serotype or isolate, so long as they function as intended, i.e., to allow for excision and rescue of the sequence of interest from a host cell genome or vector, and to allow integration of the heterologous sequence into the recipient cell genome when AAV Rep gene products are present in the cell. Additionally, AAV ITRs may be derived from any of several AAV serotypes, including without limitation, AAV-1, AAV-2, AAV-3, AAV-4, AAV 5, AAV-6, etc. Furthermore, 5' and 3' ITRs which flank a selected nucleotide sequence in an AAV expression vector need not necessarily be identical or derived from the same AAV serotype or isolate, so long as they function as intended, i. e., to allow for excision and rescue of the sequence of interest from a host cell genome or vector, and to allow integration of the DNA molecule into the recipient cell genome when AAV Rep gene products are present in the cell.

Particularly vectors are vectors derived from AAV serotypes having tropism for and high transduction efficiencies in cells of the mammalian central and peripheral nervous system, particularly neurones, neuronal progenitors, astrocytes, oligodendrocytes and glial cells. A review and comparison of transduction efficiencies of different serotypes is provided in Cearley C N et al., 2008 and Piguet et al, 2013. In other non-limiting examples, preferred vectors include vectors derived from any serotypes like AAV1, AAV2, AAV3, AAV4, AA5, AAV6, AAV7, AAV8, AAV9, or AAVrh.10, which have also been shown to transduce cells of central and peripheral nervous system.

The selected nucleotide sequence is operably linked to control elements that direct the transcription or expression thereof in the subject in vivo. Such control elements can comprise control sequences normally associated with the selected gene.

Alternatively, heterologous control sequences can be employed. Useful heterologous control sequences generally include those derived from sequences encoding mammalian or viral genes. Examples include, but are not limited to, the phosphoglycerate kinase (PKG) promoter, CAG, NSE, (neuronal specific enolase) or NeuN, the SV40 early promoter, mouse mammary tumor virus LTR promoter; adenovirus major late promoter (Ad MLP); a herpes simplex virus (HSV) promoter, a cytomegalovirus (CMV) promoter such as the CMV immediate early promoter region (CMVIE), rous sarcoma virus (RSV) promoter, synthetic promoters, hybrid promoters, and the like. The promoters can be of human origin or from other species, including from mice. In addition, sequences derived from nonviral genes, such as the murine metallothionein gene, will also find use herein. Such promoter sequences are commercially available from, e. g. Stratagene (San Diego, Calif.).

Examples of heterologous promoters include the CMV promoter.

Examples of inducible promoters include DNA responsive elements for ecdysone, tetracycline, hypoxia andaufin.

The AAV expression vector which harbors the DNA molecule of interest bounded by AAV ITRs, can be constructed by directly inserting the selected sequence (s) into an AAV genome which has had the major AAV open reading frames ("ORFs") excised therefrom. Other portions of the AAV genome can also be deleted, so long as a sufficient portion of the ITRs remain to allow for replication and packaging functions. Such constructs can be designed using techniques well known in the art. See, e. g. U.S. Pat. Nos. 5,173,414 and 5,139,941; International Publications Nos. WO 92/01070 (published 23 Jan. 1992) and WO 93/03769 (published 4 Mar. 1993); Lebkowski et al., 1988; Vincent et al., 1990; Carter, 1992; Muzyczka, 1992; Kotin, 1994; Shelling and Smith, 1994; and Zhou et al., 1994. Alternatively, AAV ITRs can be excised from the viral genome or from an AAV vector containing the same and fused 5' and 3' of a selected nucleic acid construct that is present in another vector using standard ligation techniques. AAV vectors which contain ITRs have been described in, e. g. U.S. Pat. No. 5,139,941. In particular, several AAV vectors are described therein which are available from the American Type Culture Collection ("ATCC") under Accession Numbers 53222, 53223, 53224, 53225 and 53226. Additionally, chimeric genes can be produced synthetically to include AAV ITR sequences arranged 5' and 3' of one or more selected nucleic acid sequences. Preferred codons for expression of the chimeric gene sequence in mammalian CNS and PNS cells can be used. The complete chimeric sequence is assembled from overlapping oligonucleotides prepared by standard methods. See, e. g., Edge, 1981; Nambair et al., 1984; Jay et al., 1984. In order to produce AAV virions, an AAV expression vector is introduced into a suitable host cell using known techniques, such as by transfection. A number of transfection techniques are generally known in the art. See, e. g., Graham et al., 1973; Sambrook et al. (1989) Molecular Cloning, a laboratory manual, Cold Spring Harbor Laboratories, New York, Davis et al. (1986) Basic Methods in Molecular Biology, Elsevier, and Chu et al., 1981. Particularly suitable transfection methods include calcium phosphate co-precipitation (Graham et al., 1973), direct microinjection into cultured cells (Capecchi, 1980), electroporation (Shigekawa et al., 1988), liposome mediated gene transfer (Mannino et al., 1988), lipid-mediated transduction (Felgner et al., 1987), and nucleic acid delivery using high-velocity microprojectiles (Klein et al., 1987).

For instance, a preferred viral vector, such as the AAV9 or the AAVrh.10, comprises, in addition to a FXN encoding nucleic acid sequence, the backbone of AAV vector with ITR derived from AAV-2, the promoter, such as the mouse PGK (phosphoglycerate kinase) gene or the cytomegalovirus/β-actin hybrid promoter (CAG) consisting of the enhancer from the cytomegalovirus immediate gene, the promoter, splice donor and intron from the chicken β-actin gene, the splice acceptor from rabbit β-globin, or any promoter such as PGK, CAG, NSE.

Delivery of the Vectors

It is herein provided a method for preventing and treating the neurological phenotype associated with Friedreich ataxia in a subject in need thereof, said method comprising:
(a) providing a vector as defined above, which comprises a frataxin (FXN) encoding nucleic acid; and
(b) delivering the vector to the subject in need thereof and whereby the gene of the frataxin (FXN) is expressed by the transduced cells at a therapeutically effective level.

In a particular method, based on stereotaxic delivery, the vector can be delivered directly and specifically into selected brain regions by intracerebral injections into the cerebellum, the dentate nucleus, the striatum or the hippocampus. In another particular method, the vector can be delivered by intrathecal delivery.

In a still another embodiment, the vector can be delivered directly into the brain by intracerebrally injection and in the same time in blood by intravenously injection or in the spinal fluid by intrathecal delivery.

Particularly, any routes of administration that allow an important expression of the vector in the spinal cord, brain, cortex, hippocampus, dentate nucleus and, purkinje and granular cerebellar cells can be used in the invention.

The target cells of the vectors of the present invention are cells of the CNS, in particular the cerebellum and spinal cord and PNS, in particular the dorsal root ganglia of a subject afflicted with neurological phenotype associated with Friedreich ataxia. Preferably the subject is a human being, adult or child.

However the invention encompasses delivering the vector to biological models of the disease. In that case, the biological model may be any mammal at any stage of development at the time of delivery, e.g., embryonic, fetal, infantile, juvenile or adult. Furthermore, the target neuronal cells may be essentially from any source, especially any cells derived from hiPS from FRDA patients, nonhuman primates and mammals of the orders Rodenta (mice, rats, rabbit, hamsters), Carnivora (cats, dogs), and Arteriodactyla (cows, pigs, sheep, goats, horses) as well as any other non-human system (e. g. zebrafish model system).

In one embodiment, the biological model can be a model as used in the examples like the mildly or the late symptomatic parvalbumin model (see examples).

The vectors used herein may be formulated in any suitable vehicle for delivery. For instance they may be placed into a pharmaceutically acceptable suspension, solution or emulsion. Suitable mediums include saline and liposomal preparations. More specifically, pharmaceutically acceptable carriers may include sterile aqueous of non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Intravenous vehicles include fluid and nutrient replenishers, electrolyte replenishers (such as those based on Ringer's dextrose), and the like.

Preservatives and other additives may also be present such as, for example, antimicrobials, antioxidants, chelating agents, and inert gases and the like.

A colloidal dispersion system may also be used for targeted gene delivery. Colloidal dispersion systems include macromolecule complexes, nanocapsules, microspheres, beads, and lipid-based systems including oil-in-water emulsions, micelles, mixed micelles, and liposomes.

The preferred doses and regimen may be determined by a physician, and depend on the age, sex, weight, of the subject, and the stage of the disease. As an example, for delivery of a nucleic acid sequence encoding an FXN polypeptide using a viral expression vector, each unit dosage of FXN polypeptide expressing vector may comprise 2.5 µl to 10 ml of a composition including a viral expression vector in a pharmaceutically acceptable fluid at a concentration ranging from $10^{11}$ to $10^{16}$ viral genome per ml for example.

In particular embodiments, when the vector containing a nucleic acid sequence encoding an FXN polypeptide is intracerebrally delivered, the dose is about the microliter and when the vector containing a nucleic acid sequence encoding an FXN polypeptide is intrathecally delivered, the dose is about the milliliter.

In a particular embodiment, the invention relates to a vector which comprises a FXN encoding nucleic acid for use in prevention or treatment of neurological phenotype associated with Friedreich ataxia in a subject in need thereof wherein the vector is delivering to the subject in need thereof and wherein FXN is expressed by the transduced cells at a therapeutically effective level.

Pharmaceutical Composition

A second object of the invention concerns a pharmaceutical composition for preventing or treating neurological phenotype associated with Friedreich ataxia in a subject in need thereof, which comprises a therapeutically effective amount of a vector which comprises a frataxin (FXN) encoding nucleic acid.

By a "therapeutically effective amount" is meant a sufficient amount of the vector of the invention to treat, prevent or stabilise the neurological phenotype associated with Friedreich ataxia at a reasonable benefit/risk ratio applicable to any medical treatment.

It will be understood that the single dosage or the total daily dosage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidental with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range per adult per day. The therapeutically effective amount of the vector according to the invention that should be administered, as well as the dosage for the treatment of a pathological condition with the number of viral or non-viral particles and/or pharmaceutical compositions of the invention, will depend on numerous factors, including the age and condition of the patient, the severity of the disturbance or disorder, the method and frequency of administration and the particular peptide to be used.

In one embodiment, the pharmaceutical compositions that contain the vector according to the invention can be administrated to the subject in need thereof one time, two times, three times or more on at least one day or more.

In one embodiment, the pharmaceutical compositions that contain the vector according to the invention can be administrated to the subject in need thereof one time and readministered several months or years later to said subject.

In one embodiment, the pharmaceutical compositions that contain the vector according to the invention can be administrated to the subject in need thereof by intravenous injection one time or more.

The presentation of the pharmaceutical compositions that contain the vector according to the invention may be in any form that is suitable for the selected mode of administration, for example, for intracerebrally, intracortically, intrathecal or intravenous administration.

In the pharmaceutical compositions of the present invention for intravenous, intracerebral, intracortical or intrathecal administration, the active principle, alone or in combination with another active principle, can be administered in a unit administration form, as a mixture with conventional pharmaceutical supports, to animals and human beings.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid. It must be stable under the conditions of manufacture and storage and must be preserved against the contaminating action of microorganisms, such as bacteria and fungi.

Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The vector according to the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The pharmaceutical composition will be rendered sterile using techniques well known by the man of the art. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active polypeptides in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

Multiple doses can also be administered.

In another embodiment, the pharmaceutical composition according to the invention may contain an AAV9 which comprises a nucleic acid encoding frataxin and an AAVrh.10 which also comprises a nucleic acid encoding frataxin.

In another embodiment, the pharmaceutical composition according to the invention may contain an AAV9 which comprises a nucleic acid encoding frataxin and which is administrated to a subject in need thereof intravenously or intrathecal delivery and an AAVrh.10 which also comprises a nucleic acid encoding frataxin and which is administrated to the same subject in need thereof intracerebellar or intracerebral delivery.

In other words, the invention also relates to i) an AAV9 which comprises a nucleic acid sequence encoding for the frataxin (FXN) and ii) an AAVrh.10 which comprises a nucleic acid sequence encoding for the frataxin (FXN) gene as a combined preparation for simultaneous, separate or sequential use in the prevention or treatment of neurological phenotype associated with Friedreich ataxia in a subject in need thereof wherein the AAV9 is administrated to a subject in need thereof intravenously or intrathecally and wherein the AAVrh.10 is administrated to the same subject in need thereof intracerebellar or intracerebral delivery.

In another embodiment, the pharmaceutical composition according to the invention may contain an AAVrh.10 which comprises a nucleic acid encoding frataxin and which is administrated to a subject in need thereof intravenously or intrathecal delivery and an AAV9 which also comprises a nucleic acid encoding frataxin and which is administrated to the same subject in need thereof intracerebellar or intracerebral delivery.

In other words, the invention also relates to i) an AAVrh.10 which comprises a nucleic acid sequence encoding for the frataxin (FXN) and ii) an AAV9 which comprises a nucleic acid sequence encoding for the frataxin (FXN) gene as a combined preparation for simultaneous, separate or sequential use in the prevention or treatment of neurological phenotype associated with Friedreich ataxia in a subject in need thereof wherein the AAVrh.10 is administrated to a subject in need thereof intravenously or intrathecally and wherein the AAV9 is administrated to the same subject in need thereof intracerebellar or intracerebral delivery.

The invention also relates to i) an AAV9 which comprises a nucleic acid sequence encoding for the frataxin (FXN) and ii) an AAVrh.10 which comprises a nucleic acid sequence encoding for the frataxin (FXN) gene as a combined preparation for simultaneous, separate or sequential use in the prevention or treatment of neurological phenotype associated with Friedreich ataxia in a subject in need thereof.

The invention will be further illustrated by the following figures and examples. However, these examples and figures should not be interpreted in any way as limiting the scope of the present invention.

FIGURES

FIG. 1: Prevention of sensory wave loss in Pvalb-KO mice treated with AAV9-hFXN-HA at 3.5 weeks.

(A) String test analysis, time needed to attach hindlimbs to the string is represented. (B) Amplitude of sensory wave (H-Wave) was recorded after plantar sciatic nerve stimulation. n=9 WT and n=9 untreated Pvalb-KO and n=9 treated Pvalb-KO with AAV9-CAG-hFXN-HA for each test. *$p<0.05$; $p<0.01$; *$p<0.001$; ****$p<0.0001$.

FIG. 2: Rescue of sensory wave loss in Pvalb-KO mice treated at 7.5 weeks.

(A) Notched bar test analysis, number of foot fall is represented. n=28 WT and n=31 untreated Pvalb-KO and n=31 treated Pvalb-KO with simultaneously intravenous AAV9-FXN-HA and cerebral AAVrh10-FXN-HA. Measurement of paw angle variability (B), ataxia coefficient (C) midline distance (D) after 2.5 s of walk on the DigitGait apparatus. n=8 for WT, n=6 for untreated Pvalb-KO and n=8 for post-symptomatic treated Pvalb-KO animals for the digit gait analysis. Stars correspond to p-value of untreated Pvalb-KO vs WT and treated Pvalb-KO vs untreated Pvalb-KO. *$p<0.05$; $p<0.01$; *$p<0.001$; ****$p<0.0001$. Animals were treated at 7.5 weeks of age.

FIG. 3: Prevention of neurodegeneration and loss of dorsal root ganglion neurons after treatment.

Mean number of neuron per DRG of WT and Pvalb-KO (untreated and treated) was evaluated at the lumbar level of the spinal cord at 18.5 weeks. Around 43 DRG were analyzed per group. $p<0.01$; *$p<0.001$. Stars correspond to p-value of untreated Pvalb-KO vs WT and treated Pvalb-KO vs untreated Pvalb-KO FIG. 4: Complete rescue of sensory wave loss in Pvalb-KO mice treated with AAV-hFXN-HA at 7.5 weeks.

Amplitude of sensory wave (H-Wave) was recorded after plantar sciatic nerve stimulation. N=31 WT and n=28 Pvalb-KO untreated and n=31 Pvalb-KO treated with intravenous AAV9-CAG-FXN-HA and intracerebral AAVrh.10-CAG-FXN-HA for each test. *p<0.05; p<0.01; *p<0.001; ****p<0.0001.

Figure 5:
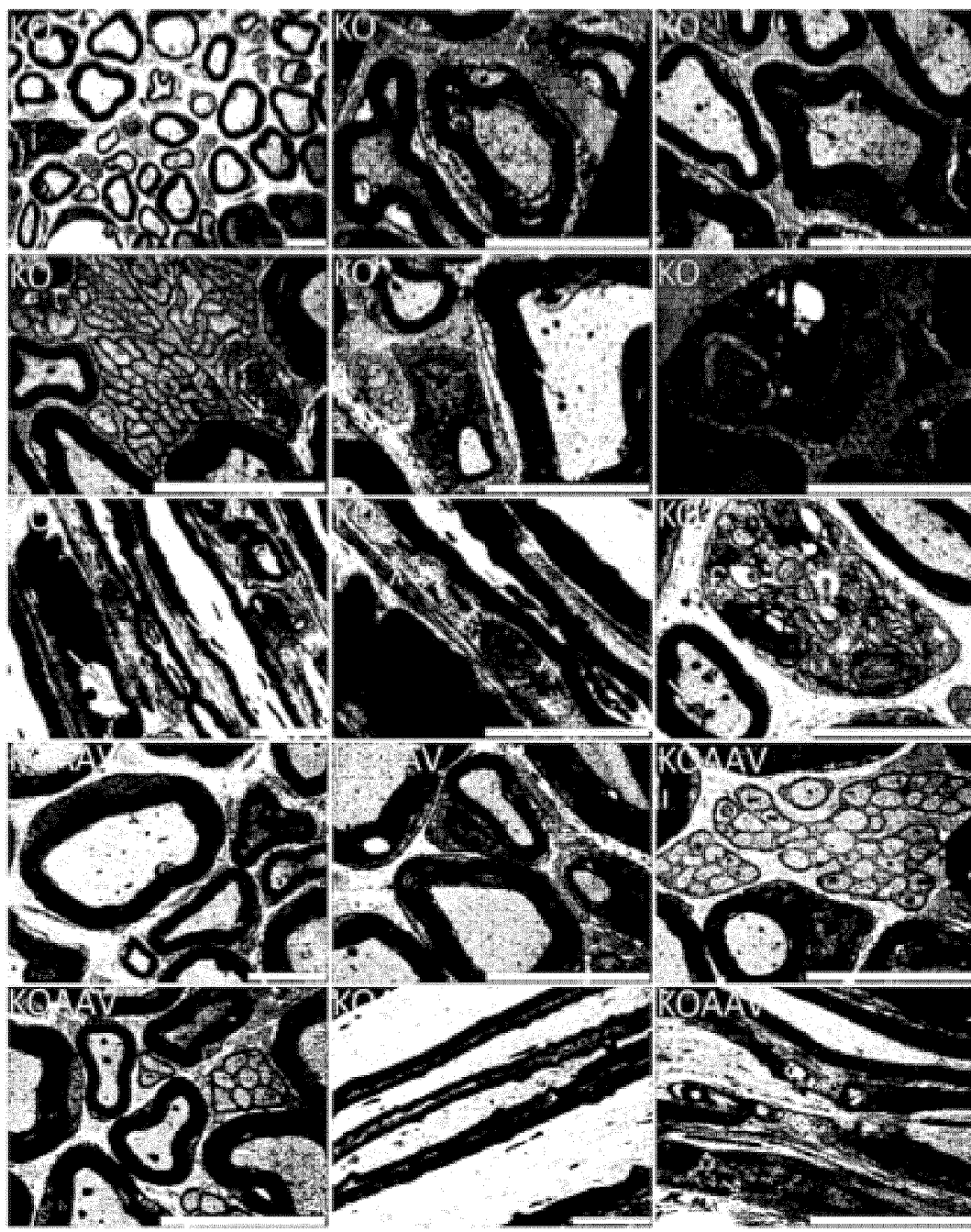

FIG. 5: Complete rescue of ultrastructure of sciatic nerves in Pvalb-KO mice treated with AAV-hFXN-HA at 7.5 weeks.

Electron microscopy analysis of transversal and longitudinal sections of sciatic nerve of Pvalb-KO animals at 20.5 weeks and Pvalb-KO animals treated with AAV-hFXN at 22.5 weeks. No abnormalities were observed in all sections observed for treated animals.

Figure 6:
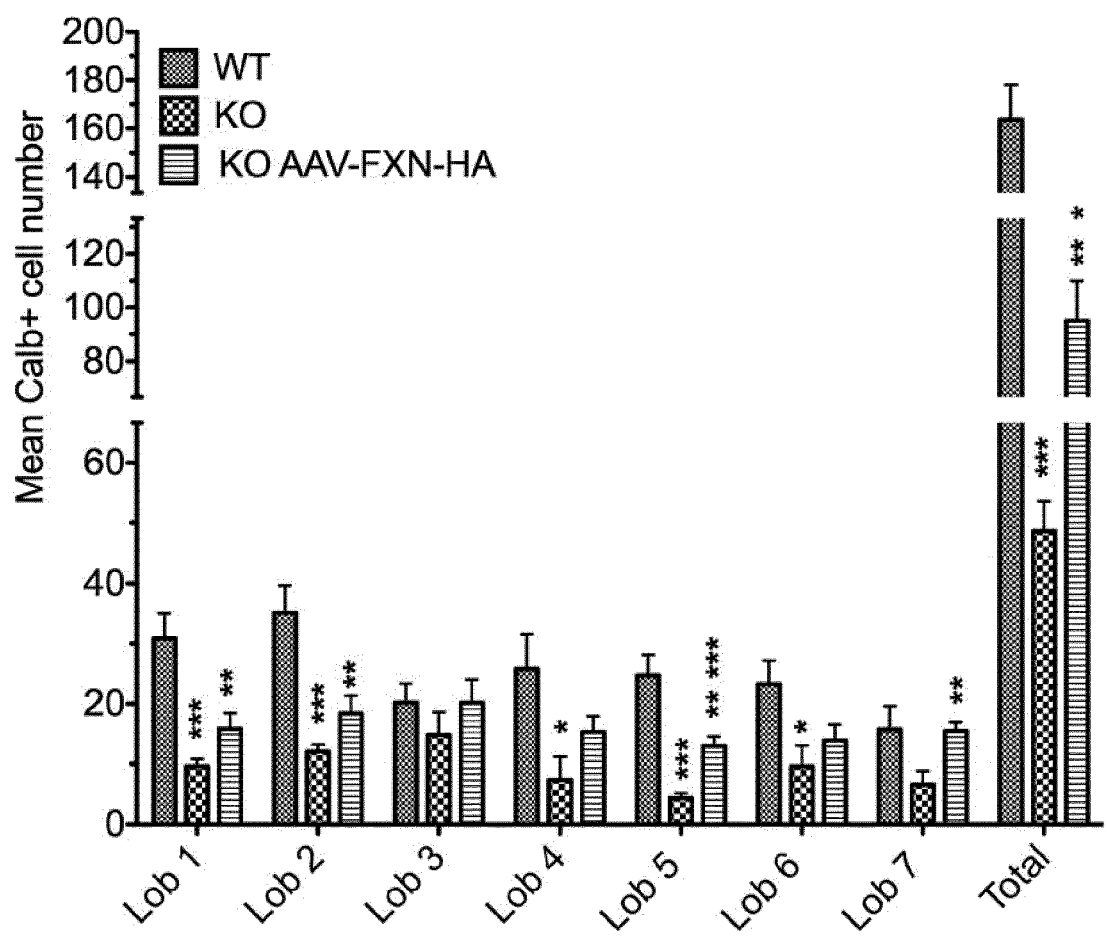

FIG. 6: Partial prevention of Purkinje cell loss after intracerebellar AAV delivery.

Mean number of calbindin positive neuron in each lobule of the cerebellum of WT and Pvalb-KO (untreated and treated) was evaluated at 18.5 weeks. Six or seven animals were analyzed per group. *p<0.05;**p<0.01. Stars correspond to p-value of untreated Pvalb-KO vs WT and treated Pvalb-KO vs untreated Pvalb-KO

EXAMPLES

Material & Methods
Adeno-Associated Virus Production

A plasmid encoding a human frataxin (hFXN) fused to a hemagglutinin (HA) tag under the control of the cytomegalovirus/β-actin hybrid promoter was produced as previously described (Perdomini et al, 2014). Both AAV9-CAG-hFXN-HA and AAVrh.10-CAG-hFXN-HA vectors were produced as previously described (Rabinowitz et al, 2002) in the Vector Core at the University Hospital of Nantes (see the website located at www(dot)vectors(dot)nantes(dot)inserm (dot)fr). The final titers of the batches used were $6.4 \times 10^{12}$ vg/ml for the AAVrh.10 and $2.5 \times 10^{13}$ vg/ml for the AAV9.

Animal Procedure

Mice with a deletion of the frataxin gene in neuronal cells ($Fxn^{L3/L-}$; $Pvalb^{Cre+}$) (Pvalb-KO) were generated and genotyped as described previously; $Fxn^{+/L3}$ mice were used as controls. Animals were maintained in a temperature and humidity controlled animal facility with a 12 h light-dark cycle and free access to water and a standard rodent chow D03 (SAFE, Villemoisson-sur-Orge, France). All animal procedures were approved by the local ethical committee (Comité d'Ethique 17, authorization number 2015050509284141 v2 (APAFIS #604)) for Animal Care and Use and were performed in accordance with the Guide for the Care and the Use of Laboratory Animals (US National Institute of Health). Both males and females were used in all experiments. For early symptomatic studies, 3.5-weeks-old mice were anesthetized using intraperitoneal injection with ketamine/xylazine (130/13 mg/kg) to allow retro orbital intravenous administration of AAV9-CAG-FXN-HA at a dose of $5 \times 10^{13}$ vg/kg diluted in NaCl 0.9% (n=9 animal treated). Untreated Pvalb-KO (n=9 animals) and WT mice (n=9 animals) were injected with equivalent volumes of saline solution. An additional group of Pvalb-KO mice was treated with a retro orbital injection of AAVrh.10-CAG-FXN-HA at a dose of $5 \cdot 10^{13}$ vg/kg (n=8 animals per group). For late symptomatic studies, 7.5-weeks-old mice were anesthetized using intraperitoneal injection with ketamine/xylazine (130/13 mg/kg) to allow positioning on the stereotactic frame (David Kopf Instruments, Tujunga, USA). Animals were injected bilaterally in the striatum and a third deposit was done in the white matter of the cerebellum, each deposit was 2 µl of virus corresponding to $1 \times 10^{10}$ vg/deposit of AAVrh.10-CAG-FXN-HA. Injections were done using a 30-gauge blunt micropipette attached to a 10 µl Hamilton syringe (Hamilton, USA) at a rate of 0.2 ul/min. The stereotactic coordinates were: AP: +0.5 mm; ML: +/−2.2 mm; DV: −3.3 mm from the bregma for injections in the striatum and AP: −6.48 mm; ML: 0 mm, DV: −2.5 mm from the bregma for the injection in the white matter of the cerebellum followed by an intravenous administration of AAV9-CAG-FXN-HA at a dose of $5 \times 10^{13}$ vg/kg. Before the wake up, animals received an injection of vetergesic (3 mg/kg), a morphinic, to avoid any suffering (Sogeval, France) (n=31 Pvalb-KO treated). Untreated Pvalb-KO (n=28 animals) and WT mice (n=31 animals) were injected with equivalent volumes of saline solution both intracerebrally and intravenously. Animals were monitored daily after the surgery.

Early symptomatic treated animals were followed until 17.5 weeks of age and late symptomatic treated animals will be followed until 20.5 weeks of age for Pvalb-KO as they display difficulties to feed properly in the home cage. The treated Pvalb-KO and WT controls were maintained until 21.5/22.5 weeks of age for the first cohort, the second and third cohorts were monitored until 18.5 weeks for all groups.

Bar-Test Analysis

Coordination and equilibrium skills were evaluated using a set of two tests: the notched bar-test for coordination and the string test which is the most sensitive to evaluate proprioception without any cerebral involvement (Deacon, 2013). Animals were scored weekly for each test from 3.5 weeks of age until euthanasia. Tests were performed in the following order: string and the notched bar-test. For each test, animals had one trial without habituation. For the notched bar test, the number of falls of the upper or lower limbs to cross the 90 cm bar was scored as well as the time to cross, and finally for the string test, the time needed by animal to attach their hindlimbs was scored. Results are presented for each test as mean±SEM for each group and t-test analyses were performed.

Digit Gait Analysis

Gait analysis was performed using a DigitGait Apparatus (Mouse specific Inc, Boston, USA) as described previously (Wooley et al, 2005). The paws of the mice were captured by video during treadmill locomotion at a speed of 8 cm/s for at least 2.5 s of proper gait and analysis was performed using the DigitGait Analyzer software (Mouse specific Inc, Boston, USA) to calculate over 40 parameters. Analysis was performed on a cohort of 8 controls and 6 Pvalb-KO and 8 treated Pvalb-KO at 17.5 weeks of age. Results are presented as mean±SEM for each group.

Rotarod Analysis

Motor capacities were tested using an accelerating rotarod LE8200 (Bioseb, France). Briefly, mice were placed each 2 or 3 weeks starting at 3.5 weeks of age on the rod for three trials/day. The rod accelerated from 4 to 40 rpm in 5 minutes. Animals were scored for their latency to fall (in seconds) for each trial and rested for 15 min between trials to avoid fatigue. Results are presented as a mean of the three trials±SEM and t-test analyses were performed.

Electromyogram Measurement

Electromyogram analyses were performed using the Keypoint apparatus (Medtronic, Minn., USA). Mice were anesthetized using intraperitoneal injection with a mix of Ketamine/xylazine (130/13 mg/kg). Animals were maintained at 37° C. during the whole experiment until wake up. Latency and amplitude of M and H waves were recorded in the plantar hind paw muscle after sciatic nerve stimulation (0.1 ms and 8 mA intensity). An additional recording of the M wave was performed in the gastrocnemius muscle. Measurements were performed each two weeks starting at 3.5 weeks of age. Results are presented as mean±SEM for each group of animals and t-test were performed.

Histology

Animals used for histology were intracardially perfused with 10 ml of Phosphate Buffer Saline (PBS) and the various tissues were dissected, fixed in PFA and embedded in paraffin. For the spinal cord analysis, the column was decalcified in ethylene-diamine-tetra acetic 0.34M, pH 7.4 (EDTA) for 14 days and the spinal cord was divided in cervical, thoracic and lumbar levels. Sequential slides (5 µm) of the paraffin blocks were stained with hematoxylin and eosin (HE).

Quantification of Neurons in DRG

Quantification of neurons in DRG was performed only at the lumbar level in KO animals. For pre-symptomatic treatment, DRG neurons were scored in 13-14 DRG per lumbar spinal cord level per animals, corresponding to at least 7600 neurons per condition and maximum 9300. For post symptomatic treatment, DRG neurons were scored in at least 43 DRG per lumbar spinal cord level per animals and two sections were scored per DRG, corresponding to at least 9500 neurons per condition and maximum 14000. Number of neurons was normalized by the area of the DRG section. Three to six mice were scored per condition and results were expressed as mean±SEM.

Electron Microscopy

Animals were intracardially perfused with 10 ml of Phosphate Buffer Saline (PBS) and the various tissues were dissected, fixed in 2.5% PFA/2.5% glutaraldehyde in cacodylate buffer. After overnight fixation, the column was decalcified in ethylene-diamine-tetra acetic 0.34M, pH 7.4 (EDTA) for 14 days and fixed for an additional overnight. Tissues were rinsed in PBS, postfixed in 1% osmium tetroxide for 2 h at room temperature, dehydrated and embedded in Epon. Regions of interest were localized on 2 µm sections stained with toluidine blue. Ultrathin sections (70 nm) were stained with uranyl acetate and lead citrate and observed with a Morgagni 268D electron microscopy.

Purkinje Cell Quantification

Purkinje cells were stained with calbindin staining. For all histological studies, phosphate buffer saline (PBS) used was supplemented with CaCl2 and MgCl2. Paraffin was removed from the slides and permeabilization was performed for 30 min in PBS-Triton 0.3% and then blocking for 1 h at room temperature in PBS-Triton 0.1%-NGS 5%. Rabbit anti calbindin antibody (1:500, Swan laboratories) was incubated overnight at 4° C. After 3 washes, anti-rabbit antibody coupled to alexafluor 488 (Invitrogen) was incubated for 1 h at room temperature. After washes, slides were mounted using Vectashield medium with Dapi (Vector). Quantification was achieved on 5 slides of cerebellum per animal and mean calbindin number was scored in each lobules of the cerebellum.

Gene Expression Analysis

All tissues except DRG, sciatic nerve and hippocampus were crushed in liquid nitrogen and powder was maintained at −80° C. Total RNA was extracted from DRG frozen tissues pulverized with a Precellys24 homogenizer (Bertin Technologies) using Trizol reagent (MRC) according to the manufacturer's protocol and was extracted with DNAse I (Roche Biosciences). cDNA was generated by reverse transcription using the Transcriptor first-strand cDNA synthesis kit (Roche Biosciences). Quantitative RT-PCR was performed using the SYBR Green I Master mix (Roche Biosciences) and Light Cycler 480 (Roche Biosciences) as previously described (Perdomini et al., 2014). Gapdh was used as an internal control for all samples except for sciatic nerve extracts for which we used 18S due to variation in Gapdh expression in controls and KO animals. Each samples was analyzed in duplicate and at least 3 mice were analyzed per condition.

VGC Determination

DNA was extracted using a classical Phenol/chloroform protocol. AAV9-CAG-FXN-HA or AAVrh.10-CAG-FXN-HA vector genome copy numbers were measured by quantitative PCR in the DRG, spinal cord (cervical, thoracic and lumbar levels), brain, cerebellum, heart and liver using the Light Cycler 480 II (Roche, France) and the Light cycler 480 SYBR Green I Master (Roche, France) as previously described (Perdomini et al 2014). Vector sequences and mouse genomic Adck3 (internal control) sequences were simultaneously amplified. The results (vector genome copy number per cell, VGC) were expressed as n-fold differences in the transgene sequence copy number relative to the Adck3 gene copy (number of viral genome copy for 2N genome). Samples were considered vector negative if transgene sequence Ct value was >35. Each sample was analyzed in duplicate.

Human Frataxin Quantification

Human frataxin was quantified in DRG samples using the human frataxin ELISA kit (Abcam). 525 ng lysates, resulting of lysate of 5DRG were loaded per well and each sample was analyzed in duplicate. A scale ranging from 0 to 800 pg/ml of recombinant hFXN was used to established standard. Final quantity was expressed as pg of human frataxin per mg of total protein.

Statistical Analyses

All data are presented as mean±SEM. Statistical analysis was carried out using GraphPad Prism software (La Jolla, USA). t-test were used to compare group and a value of $p<0.05$ was considered as significant.

Results

Intravenous Injection of AAVrh.10-CAG-hFXN-HA Slightly Delays the Phenotype Develop by Pvalb-KO Mice As intravenous injection of AAVrh10-CAG-FXN-HA was previously shown to prevent and rescue the cardiomyopathy in the cardiac model of FRDA (Perdomini et al, 2014), we wanted to investigate whether it could have a therapeutical benefit on the neurological phenotype in the Pvalb-KO mice. AAVrh.10-CAG-FXN-HA was previously reported to transduce DRG after intravenous injection (Perdomini et al., 2014). While intravenous delivery of $5 \times 10^{13}$ vg/kg of AAVrh.10-CAG-FXN-HA slightly delayed the onset of the neurological phenotype in treated animals, by 7.5 weeks of age, the treated animal clearly started to develop a coordination phenotype on both bar test and string (data not shown). Behavioral scores were indistinguishable to untreated animals at the time of sacrifice (17.5 weeks), except for the rotarod test which showed some prevention (data not shown). In accordance with the behavioral results, animals treated with the AAVrh.10-CAG-FXN-HA displayed a slight delayed loss in H-wave but a complete loss of H-wave was observed at the end of the protocol (data not shown). In agreement with the phenotype we observed, AAVrh.10-CAG-FXN-HA treatment did not prevent the neuronal loss within lumbar DRG (data not shown). Ultrathin sections of sciatic nerves of AAVrh.10-CAG-FXN-HA treated Pvalb-KO mice still displayed signs of degeneration, axonal shrinkage, autophagic vacuoles, although not as pronounced as in untreated Pvalb-KO animals (data not shown). Together, these results demonstrate that intravenous injection of AAVrh.10-CAG-FXN-HA at $5\times10^{13}$ vg/kg can only slightly delay the onset of the loss of coordination and sensory neuropathy in Pvalb-KO mice.

Prevention of Progressive Loss of Sensory Defects after Treatment of Early-Symptomatic Pvalb-KO Mice with Intravenous AAV9-CAG-FXN-HA Injection Pvalb-KO mice treated at 3.5 weeks of age already showed a moderate but significant impairment at the notched bar test prior to treatment as described previously (data not shown). Intravenous delivery of AAV9-CAG-FXN-HA allowed a significant coordination improvement in treated Pvalb-KO mice compare to Pvalb-KO untreated mice (data not shown). When mice where submitted to the string test, Pvalb-KO treated mice remained undistinguishable from WT controls until euthanasia (FIG. 1A) showing a clear benefit of the treatment on the pathology. Notched bar test revealed an intermediate situation of the Pvalb-KO treated mice, with a recovery or prevention until 8.5 weeks of age (data not shown). As trembling was observed in all mice, this impairment could be related to a cerebral affection developed by Pvalb-KO mice, which is poorly corrected by intravenous delivery of AAV9. AAV9 is known to have a limited diffusion across the blood-brain barrier and poor neuronal transduction in brain after P21 in mice. Similarly, rotarod analysis showed a significant prevention of the loss of coordination in treated mice compare to untreated Pvalb-KO (data not shown).

To validate the behavioral prevention of the phenotype and evaluate function of sensory fibers, electromyographic analyses were performed. Prevention of sensory wave (H-Wave) loss was observed in Pvalb-KO treated animals from 4.5 weeks of age up to euthanasia (FIG. 1B). As previously described Pvalb-KO mice did not show any abnormalities in motor wave, both after plantar or gastrocnemian stimulation (data not shown).

Due to significant trembling, animals were sacrificed at 17.5 weeks of age for histological and molecular analysis. Scoring of DRG neurons revealed a complete prevention of neurons loss in Pvalb-KO treated animals both at cervical and lumbar level (data not shown). Preliminary results of electron microscopy analysis, revealed a prevention of structural abnormalities and mitochondrial degeneration in DRG observed in Pvalb-KO at 17.5 weeks after AAV9-CAG-FXN-HA treatment (data not shown). Moreover, ultrastructural analysis of sciatic nerve, composed of mixed motor and sensitive fibers, as well as the saphenous nerve, composed purely of sensory fibers, revealed a complete prevention of abnormalities observed in untreated Pvalb-KO mice (data not shown). No sign of degeneration, axonal loss, nor autophagy are observed in Pvalb-KO treated mice, neither in sciatic nor saphenous nerves (data not shown).

As expected, a decreased level of mFXN mRNA was observed in the DRG, cervical, thoracic and lumbar levels of the spinal cord, brain, cerebellum, heart and liver at 17.5 weeks (data not shown). Biodistribution study of the AAV9-FXN-HA vector reveals a large transduction of the liver, heart and brain, a moderate transduction of the DRG and quite poor of the spinal cord and cerebellum (data not shown). Evaluation of hFXN mRNA levels revealed high expression of transgene in DRG, brain, heart and liver and to a lesser extent in cerebellum and spinal cord (data not shown).

Simultaneous Intracerebellar and Intravenous Treatment in Late Symptomatic Pvalb-KO Mice Corrects the Sensory Ataxia and Improve the Cerebral/Cerebellar Component Develop by Pvalb-KO Mice At diagnosis, FA patients already displayed coordination impairment and a severe loss of sensory nerve conduction. Considering the very promising results obtained in early symptomatic Pvalb-KO mice, we wanted to evaluate whether our therapeutic strategy could also lead to any benefit in a post-symptomatic treatment. For this purpose, another set of mice (divided in 3 cohorts) was treated post-symptomatically at 7.5 weeks of age, an age with a clear loss of coordination and sensory conduction defect. To try to correct the cerebellar and cerebral components developed in Pvalb-KO mice, treated mice also received three intracerebral deliveries of AAVrh.10-CAG-FXN-HA, bilaterally in the striatum, known to lead to a widespread diffusion of the vector to several structures including the hippocampus and interneurons of the cortex and the corpus callosum (Piguet et al, 2013), and into the cerebellar white matter to allow a large transduction of cerebellum (data not shown). AAVrh.10-CAG-GFP injection clearly show a broader transduction of neurons after stereotactic delivery in mice compared to AAV9-CAG-GFP (data not shown).

As previously described, at 7.5 weeks of age, Pvalb-KO mice already displayed impairments when challenged for behavioral analyses in all tests (FIG. 2A). The simultaneous intracerebral and intravenous AAV-CAG-FXN-HA treatment led to a significant improvement of behavior in only one week. A complete correction of the phenotype was observed at the string test (more specific for proprioception) only one week after injection and a prevention of any deterioration was shown up to euthanasia (FIG. 2A). For notched bar test, Pvalb-KO treated mice show a clear improvement of the phenotype over time compare to untreated animals, a milder improvement is observed at the rotarod test (data not shown). Evaluation of gait at 17.5 weeks of age showed a complete correction of several parameters affected in the untreated Pvalb-KO ataxic animals, including paw angle variability, paw placement and mid line distance (FIG. 2B-D). For the first cohort, untreated Pvalb-KO mice were euthanized at 20.5 weeks of age because of their incapacity to move in the cage and therefore to feed themself properly. WT and treated Pvalb-KO mice were euthanized at 22.5 and 21.5 weeks of age due to spontaneous loss of several treated animals probably as a consequence of an epileptic attack, due to deletion of frataxin in cerebral interneurons and hippocampus (a phenotype not relevant to FRDA patient, but as a flaw of the model). For the second and third cohort, we sacrificed all animals at 18.5 weeks of age to avoid any epileptic seizures and loss of animals. Concomitantly with the improvement of behavior, Pvalb-KO mice displayed a complete reversion of sensory wave loss (FIG. 3), H-wave amplitude, which was already strongly decreased before treatment (FIG. 3). The treated animals were indistinguishable to controls, coherent with a complete reversion of sensory defect in Pvalb-KO treated mice. No change were observed in the motor wave, nor plantar nor gastrocnemian (data not shown). We scored the mean number of DRG neurons in the second and third cohorts of treatment at 18.5 weeks of age, only at the lumbar level as we did not previously observed any neuronal loss in the thoracic and cervical portions. Scoring of DRG neurons revealed a complete prevention of neurons loss in Pvalb-KO treated animals at lumbar level compared to untreated Pvalb-KO mice, which display a 14% neuronal loss (FIG. 3).

Figure 4:
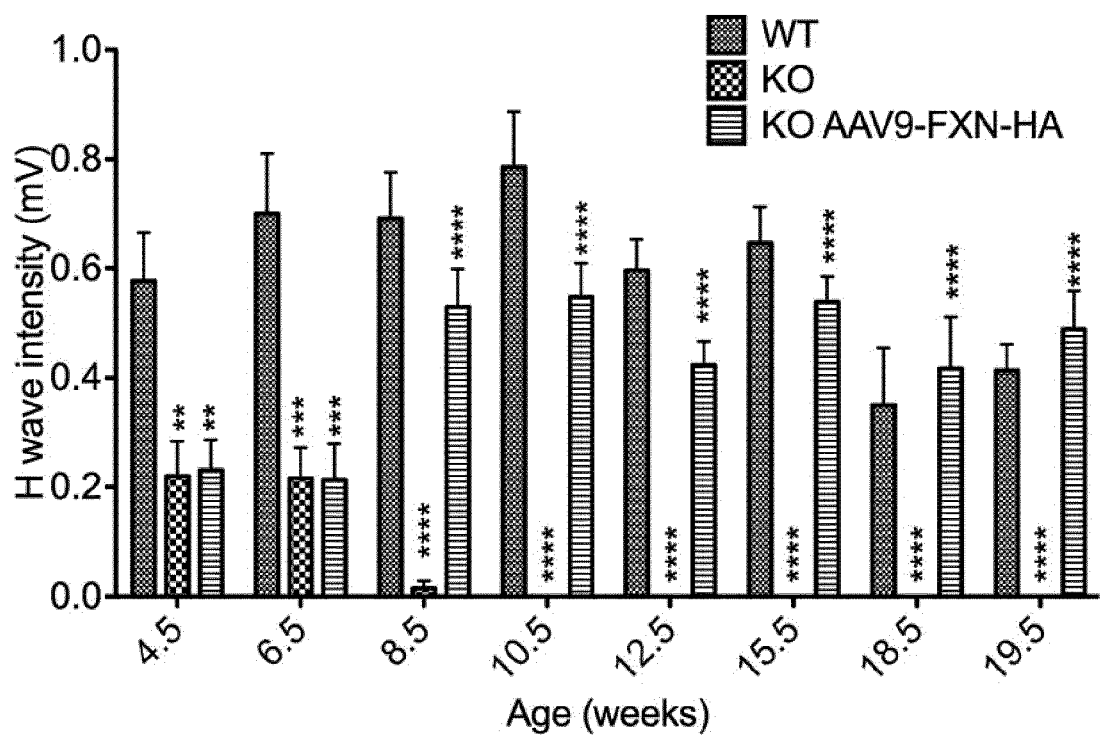

Analysis of peripheral nerves revealed a complete correction of ultrastructure of both sciatic and saphenous nerve structure in treated animals at 22.5 and 21.5 weeks respectively, nerves which already displayed abnormalities at 7.5 weeks of age when animals were treated (FIG. 4 and data not shown).

As behavioral analyses of our treated animals already showed a clear improvement one-week post injection, we wondered whether structure of the sciatic and saphenous nerves would already be affected and could be corrected. Ultrathin sections of both sciatic and saphenous nerve (data not shown) demonstrate that untreated animals already displayed signs of axonal regeneration (data no shown). Interestingly, and in agreement with the behavioral studies, our results demonstrate a clear improvement one week after treatment compare to non-treated animals.

These data correlates with the kinetic study of human frataxin expression that we performed upon intravenous AAV9-FXN delivery in WT animals. As soon as 3 days following the injection, significant expression of human frataxin is already detected (data not shown).

Biodistribution study of both AAV9-FXN-HA and AAVrh.10-FXN-HA vector was performed both for the final study at 22.5 weeks of age as well as 7 days post injection (data not shown). Liver and brain are largely transduced; heart, DRG and spinal cord to a lesser extend correlating with previous data we obtained (data not shown). Evaluation of hFXN mRNA levels (data not shown) revealed high expression of transgene in heart and liver. Even if brain contains more VGC than DRG, we have similar expression in both tissues and spinal cord express human frataxin to a lesser extent (data not shown).

Aged Pvalb KO mouse display strong Purkinje cell loss (Piguet, de Montigny et al, in preparation). To prevent this massive loss, we delivered AAVrh.10-AAV-FXN in the white matter of the cerebellum to maximize the diffusion within the cerebellum. At 18.5 weeks of age, we scored the mean number of Purkinje cells in each lobule of the cerebellum for each group of mice. AAV delivery clearly prevent Purkinje cell loss, compare to untreated animals (FIG. 6). We observed variability from one lobule to the other, with better prevention of neuronal loss in lobules 3, 4, 5 and 7 than lobule 1 or 2 or 6, this mainly due to the diffusion of the AAV following the intracerebellar delivery.

REFERENCES

Throughout this application, various references, including United States patents and patent applications, describe the state of the art to which this invention pertains. The disclosures of these references are hereby incorporated by reference in entirety into the present disclosure.

Adinolfi, S., C. Iannuzzi, et al. (2009). "Bacterial frataxin CyaY is the gatekeeper of iron-sulfur cluster formation catalyzed by IscS." Nat Struct Mol Biol 16(4): 390-396.

Cavadini, P., J. Adamec, et al. (2000). "Two-step processing of human frataxin by mitochondrial processing peptidase. Precursor and intermediate forms are cleaved at different rates." J Biol Chem 275(52): 41469-41475.

Cearley C N, Vandenberghe L H, Parente M K, Carnish E R, Wilson J M, Wolfe J H. Expanded repertoire of AAV vector serotypes mediate unique patterns of transduction in mouse brain. Mol Ther. 2008 October; 16(10):1710-8. doi: 10.1038/mt.2008.166. Epub 2008 Aug. 19.

Condo, I., N. Ventura, et al. (2007). "In vivo maturation of human frataxin." Hum Mol Genet 16(13): 1534-1540.

Colin F, Martelli A, Clémancey M, Latour J M, Gambarelli S, Zeppieri L, Birck C, Page A, Puccio H, Ollagnier de Choudens S. Mammalian frataxin controls sulfur production and iron entry during de novo Fe4S4 cluster assembly. J Am Chem Soc. 2013 Jan. 16; 135(2):733-40. doi: 10.1021/ja308736e. Epub 2013 Jan. 7.

Deutsch, E. C., A. B. Santani, et al. (2010). "A rapid, noninvasive immunoassay for frataxin: utility in assessment of Friedreich ataxia." Mol Genet Metab 101(2-3): 238-245.

Harding A E. Friedreich's ataxia: a clinical and genetic study of 90 families with an analysis of early diagnostic criteria and intrafamilial clustering of clinical features. Brain. 1981 September; 104(3):589-620.

Huynen, M. A., B. Snel, et al. (2001). "The phylogenetic distribution of frataxin indicates a role in iron-sulfur cluster protein assembly." Hum Mol Genet 10(21): 2463-2468.

Koeppen A H1, Mazurkiewicz J E. Friedreich ataxia: neuropathology revised. J Neuropathol Exp Neurol. 2013 February; 72(2):78-90. doi: 10.1097/NEN.0b013e31827e5762.

Koutnikova, H., V. Campuzano, et al. (1998). "Maturation of wild-type and mutated frataxin by the mitochondrial processing peptidase." Hum Mol Genet 7(9): 1485-1489.

Muhlenhoff, U., N. Richhardt, et al. (2002). "The yeast frataxin homolog Yfh1p plays a specific role in the maturation of cellular Fe/S proteins." Hum Mol Genet 11(17): 2025-2036.

Piguet F, Sondhi D, Piraud M, Fouquet F, Hackett N R, Ahouansou O, Vanier M T, Bieche I, Aubourg P, Crystal R G, Cartier N, Sevin C. Correction of brain oligodendrocytes by AAVrh.10 intracerebral gene therapy in metachromatic leukodystrophy mice. Hum Gene Ther. 2012 August; 23(8):903-14. doi: 10.1089/hum.2012.015. Epub 2012 Jul. 23.

Schmucker, S., M. Argentini, et al. (2008). "The in vivo mitochondrial two-step maturation of human frataxin." Hum Mol Genet 17(22): 3521-3531.

Schmucker, S., A. Martelli, et al. (2011). "Mammalian frataxin: an essential function for cellular viability through an interaction with a preformed ISCU/NFS1/ISD11 iron-sulfur assembly complex." PLoS One 6(1): e16199.

Tsai, C. L. and D. P. Barondeau (2010). "Human frataxin is an allosteric switch that activates the Fe—S cluster biosynthetic complex." Biochemistry 49(43): 9132-9139.

The invention claimed is:

1. A method for inhibiting, preventing and/or treating a neurological phenotype associated with Friedreich's ataxia in a subject in need thereof, comprising
    administering to said subject a therapeutically effective amount of at least one vector, selected from the group consisting of AAV9 and AAVrh.10, which comprises a frataxin (FXN) encoding nucleic acid sequence that encodes an amino acid sequence consisting of SEQ ID NO:2,
    wherein the step of administering comprises
        i) a first step of intravenous or intrathecal administration,
        and
        ii) a second step of intracerebral injection,
    wherein the first and second steps of administering are performed simultaneously, separately or sequentially,
    wherein expression of said at least one vector persists for at least 22.5 weeks, and
    wherein sensori-motor functions and cell survival of sciatic nerves, saphenous nerve, dorsal root ganglia, and Purkinje cells are restored or preserved.

2. The method of claim 1, wherein said FXN encoding nucleic acid encodes for the amino acid sequence consisting of amino acids 81 to 210 of SEQ ID NO:2.

3. The method of claim 1, wherein the at least one vector includes an AAV 9 vector and an AAVrh.10 vector, and the step of administering is performed by administering the AAV 9 vector and the AAVrh.10 vector simultaneously, separately or sequentially.

4. The method of claim 1, wherein the intracerebral injection is performed multiple times.

5. The method of claim 1, wherein the neurological phenotype associated with Friedreich's ataxia is inhibited or prevented.

6. The method of claim 1, wherein the first step of intravenous or intrathecal administration of the AAV9 vector is intrathecal.

7. The method of claim 1, wherein the vector further comprises sequences encoding a mitochondrion-targeting signal (MTS).

8. The method of claim 7, wherein the MTS is a positively-charged N-terminal pre-sequence of 15 to 100 amino acid residues comprising arginine, leucine, serine and alanine, and said positively-charged MTS is able to form an amphiphilic alpha-helix.

9. The method of claim 1, wherein the intracerebral injection is delivered directly into a brain region selected from the group consisting of cerebellum, dentate nucleus, hippocampus and striatum of the hippocampus.

10. A method of inhibiting, preventing and/or treating one or more of i) early-symptomatic sensori-motor defects and degeneration of the dorsal root ganglia; and/or ii) post-symptomatic neurological sensori-motor defects, degeneration of the dorsal root ganglia and cerebellar dysfunction/degeneration caused by Friedreich's ataxia, comprising
administering to said subject a therapeutically effective amount of an AAVrh.10 vector and an AAV9 vector, each of which comprises a frataxin (FXN)-encoding nucleic acid sequence, wherein the FXN-encoding nucleic acid sequence encodes an amino acid sequence consisting of positions 81 to 210 of SEQ ID NO:2,
wherein the step of administering comprises
a first step of intravenous or intrathecal administration of the AAV9 vector,
and
a second step of intracerebral injection of the AAVrh.10 vector;
wherein the first and second steps of administering are performed simultaneously, separately or sequentially in any order,
wherein expression of the AAV9 vector and AAVrh.10 vector persists for at least 22.5 weeks, and
wherein one or more of the subject's sensori-motor defects are inhibited, the degeneration of the dorsal root ganglion is prevented or restored and cerebellar dysfunction/degeneration is prevented or restored.

11. The method of claim 10, wherein the intracerebral injection is delivered directly into a brain region selected from the group consisting of cerebellum, dentate nucleus, hippocampus and striatum of the hippocampus.

* * * * *

SEQUENCE LISTING

```
<160> NUMBER OF SEQ ID NOS: 2

<210> SEQ ID NO 1
<211> LENGTH: 7163
<212> TYPE: DNA
<213> ORGANISM: Homo sapiens
```

<400> SEQUENCE: 1

```
agtctccctt gggtcagggg tcctggttgc actccgtgct ttgcacaaag caggctctcc      60
attttttgtta aatgcacgaa tagtgctaag ctgggaagtt cttcctgagg tctaacctct    120
agctgctccc ccacagaaga gtgcctgcgg ccagtggcca ccaggggtcg ccgcagcacc    180
cagcgctgga gggcggagcg ggcggcagac ccggagcagc atgtggactc tcgggcgccg    240
cgcagtagcc ggcctcctgg cgtcacccag cccagcccag cccagaccc tcacccgggt     300
cccgcggccg gcagagttgg ccccactctg cggccgccgt ggcctgcgca ccgacatcga    360
tgcgacctgc acgccccgcc gcgcaagttc gaaccaacgt ggcctcaacc agatttggaa    420
tgtcaaaaag cagagtgtct atttgatgaa tttgaggaaa tctggaactt tgggccaccc    480
aggctctcta gatgagacca cctatgaaag actagcagag gaaacgctgg actctttagc    540
agagttttt gaagaccttg cagacaagcc atacacgttt gaggactatg atgtctcctt     600
tgggagtggt gtcttaactg tcaaactggg tggagatcta ggaacctatg tgatcaacaa    660
gcagacgcca aacaagcaaa tctggctatc ttctccatcc agtggaccta agcgttatga    720
ctggactggg aaaaactggg tgtactccca cgacggcgtg tccctccatg agctgctggc    780
cgcagagctc actaaagcct taaaaaccaa actggacttg tcttccttgg cctattccgg    840
aaaagatgct tgatgcccag ccccgtttta aggacattaa aagctatcag gccaagaccc    900
cagcttcatt atgcagctga ggtctgtttt ttgttgttgt tgttgtttat ttttttatt     960
cctgcttttg aggacagttg ggctatgtgt cacagctctg tagaaagaat gtgttgcctc   1020
ctaccttgcc cccaagttct gattttaat ttctatggaa gatttttgg attgtcggat    1080
ttcctcccte acatgatacc ccttatcttt tataatgtct tatgcctata cctgaatata    1140
acaacccttta aaaagcaaa ataataagaa ggaaaaattc caggagggaa atgaattgt    1200
cttcactctt cattctttga aggatttact gcaagaagta catgaagagc agctggtcaa    1260
cctgctcact gttctatctc caaatgagac acattaaagg gtagcctaca aatgttttca    1320
ggcttctttc aaagtgtaag cacttctgag ctctttagca ttgaagtgtc gaaagcaact    1380
cacacgggaa gatcatttct tatttgtgct ctgtgactgc caaggtgtgg cctgcactgg    1440
gttgtccagg gagacctagt gctgtttctc ccacatattc acatacgtgt ctgtgtgtat    1500
atatatttt tcaatttaaa ggttagtatg gaatcagctg ctacaagaat gcaaaaaatt    1560
tccaaagaca agaaaagagg aaaaaaagcc gttttcatga gctgagtgat gtagcgtaac    1620
aaacaaaatc atggagctga ggaggtgcct tgtaaacatg aagggggcaga taaggaagg    1680
agatactcat gttgataaag agagccctgg tcctagacat agttcagcca caaagtagtt    1740
gtcccttgt ggacaagttt cccaaattcc ctggacctct gcttccccat ctgttaaatg    1800
agagaataga gtatggttga ttcccagcat tcagtggtcc tgtcaagcaa cctaacagct    1860
agttctaatt ccctattggg tagatgaggg gatgacaaag aacagtttt aagctatata    1920
ggaaacattg ttattggtgt tgccctatcg tgatttcagt tgaattcatg tgaaaataat    1980
agccatcctt ggcctggcgc ggtggctcac acctgtaatc ccagcacttt tggaggccaa    2040
ggtgggtgga tcacctgagg tcaggagttc aagaccagcc tggccaacat gatgaaaccc    2100
gtctctacta aaaatacaaa aaattagccg ggcatgatgg caggtgcctg taatcccagc    2160
tacttgggag gctgaagcgg aagaatcgct tgaacccaga ggtggaggtt gcagtgagcc    2220
gagatcgtgc cattgcactg taacctgggt gactgagcaa aactctgtct caaaataata    2280
ataacaatat aataataata atagccatcc tttattgtac ccttactggg ttaatcgtat    2340
```

```
tataccacat taccctcattt taattttttac tgacctgcac tttatacaaa gcaacaagcc    2400
tccaggacat taaaattcat gcaaagttat gctcatgtta tattattttc ttacttaaag    2460
aaggatttat tagtggctgg gcatggtggc gtgcacctgt aatcccaggt actcaggagg    2520
ctgagacggg agaattgctt gaccccaggc ggaggaggtt acagtgagtc gagatcgtac    2580
ctgagcgaca gagcgagact ccgtctcaaa aaaaaaaaaa aggagggttt attaatgaga    2640
agtttgtatt aatatgtagc aaaggctttt ccaatgggtg aataaaaaca cattccatta    2700
agtcaagctg ggagcagtgg catataccta tagtcccagc tgcacaggag gctgagacag    2760
gaggattgct tgaagccagg aattggagat cagcctgggc aacacagcaa gatcctatct    2820
cttaaaaaaa gaaaaaaaaa cctattaata ataaacagt ataaacaaaa gctaaatagg    2880
taaaatattt tttctgaaat aaaattattt tttgagtctg atggaaatgt ttaagtgcag    2940
taggccagtg ccagtgagaa aataaataac atcatacatg tttgtatgtg tttgcatctt    3000
gcttctactg aaagtttcag tgcaccccac ttacttagaa ctcggtgaca tgatgtactc    3060
ctttatctgg gacacagcac aaaagaggta tgcagtgggg ctgctctgac atgaaagtgg    3120
aagttaagga atctgggctc ttatggggtc cttgtgggcc agcccttcag gcctatttta    3180 cttttcatttt acatatagct ctaattggtt tgattatctc gttcccaagg cagtgggaga    3240 tccccatttta aggaaagaaa aggggcctgg cacagtggct catgcctgta atcccagcac    3300
tttgggaggc tgaggcaagt gtatcacctg aggtcaggag ttcaagacca gcctggccaa    3360
catggcaaaa tcccgtctct actaaaaata ttaaaaaatt ggctgggcgt ggtggttcgt    3420
gcctataatt tcagctactc aggaggctga ggcaggagaa tcgctgtaac ctgggggggtg    3480 gaggttgcag tgagacgaga tcatgccact tcactccagc ctggccaaca gagccaactc    3540
cgtctcaaat aaataaataa ataaataaag ggacttcaaa cacatgaaca gcagccaggg    3600
gaagaatcaa aatcatattc tgtcaagcaa actggaaaag taccactgtg tgtaccaata    3660
gcctccccac cacagaccct gggagcatcg cctcatttat ggtgtggtcc agtcatccat    3720
gtgaaggatg agtttccagg aaaaggttat taaatattca ctgtaacata ctggaggagg    3780
tgaggaattg cataatacaa tcttagaaaa ctttttttttc ccctttctat ttttttgagac    3840 aggatctcac tttggcactc aggctggagg acagtggtac aatcaaagct catggcagcc    3900
tcgacctccc tgggcttggg caatcctccc acaggtgtgc acctccatag ctggctaatt    3960
tgtgtatttt ttgtagagat ggggtttcac catgttgccc aggctggtct ctaacactta    4020
ggctcaagtg atccacctgc ctcgtcctcc caagatgctg ggattacagg tgtgtgccac    4080
aggtgttcat cagaaagctt tttctattat ttttaccttc ttgagtgggt agaacctcag    4140
ccacatagaa aataaaatgt tctggcatga cttatttagc tctctggaat tacaaagaag    4200
gaatgaggtg tgtaaaagag aacctggggtt tttgaatcac aaatttagaa tttaatcgaa    4260
actctgcctc ttacttgttt gtagacactg acagtggcct catgttttttt tttttttttaa    4320 tctataaaat ggagatatct aacatgttga gcctgggccc acaggcaaag cacaatcctg    4380
atgtgagaag tactcagttc atgacaactg ttgttctcac atgcatagca taatttcata    4440
ttcacattgg aggacttctc ccaaaatatg gatgacgtta cctactcaac cttgaactta    4500
atcaaaatac tcagtttact taacttcgta ttagattctg attccctgga accatttatc    4560 gtgtgccttta cctgcttat attttacttg atctttttgca tacctttctaa aactatttta    4620 gccaatttaa aatttgacag tttgcattaa attataggtt tacaatatgc tttatccagc    4680
```

-continued

```
tatacctgcc ccaaattctg acagatgctt ttgccacctc taaaggaaga cccatgttca    4740
tagtgatgga gtttgtgtgg actaaccatg caaggttgcc aaggaaaaat cgctttacgc    4800
ttccaaggta cacactaaga tgaaagtaat tttagtccgt gtccagttgg attcttggca    4860
catagttatc ttctgctaga acaaactaaa acagctacat gccagcaagg gagaaagggg    4920
aaggagggc aaagttttga aatttcatgt aaatttatgc tgttcaaaac gacgagttca     4980
tgactttgtg tatagagtaa gaaatgcctt ttctttttg agacagagtc ttgctctgtc     5040
acccaggctg gagtgcagtg gcacgatctg ggctcactac aacctccgcc tcctgggttc    5100
aagcaattct ctgcctcagc ctcccgagta gctgggatta caggtgcctg ccaccacacc    5160
cggctaattt ttgtattttt agtagagacg gggtttcacc atcatggcca ggctggtctt    5220
gaactcctga cctagtaatc cacctgcctc cgcctcccaa agtgctggga ttacaggcgt    5280
gagccactgc acccagccag aaatgccttc taatctttgg tttatcttaa ttagccagga    5340
cacttggagt gcatcccgaa gtacctgatc agtggcccct ttggaatgtg taaaactcag    5400
ctcacttata tccctgcatc cgctacagag acagaatcca agctcatatg ttccatcttc    5460
tctggctgta tagtttaagg aatggaaggc accagaacag atttattgaa atgtttatta    5520
gctgaagatt tatttagaca gttgaggaaa acatcagcac ccagcagtaa aattggctct    5580
caaagatttt cttctcctgt ggaaagtcag acctctgagg ccccatccag gtagaagtac    5640
tagtgcaaga agggcctctg ctgtccactt gtgtttctgt gatctgtggg aacattgtta    5700
acgccacatc ttgacctcaa attgtttagc tcctggccag acacggtggc tcacacctgt    5760
aatcccagca ctttgagagg ctgaggcagg tggatcacct gaggttagga gttcgaggcc    5820
agcctggtca acatggtaaa accccgcctc tactaaaaat acaaaaatta gctggccgta    5880
gtggcgcacg cctgttatcc cagctactcg ggaggctgag gcaggagaat tgcttgaacc    5940
tgggtggtgg aggttgcagt gagccgagat tacaccactg cactccagcc tgggtgacaa    6000
gagggaaact ccattaaaaa aatgtaattc ccgtgtctgc catcttaagt gtaaaggtgg    6060
ctaaattata tagaaaaata agacaatatc atttcccaat tacattcctt tcctaccgca    6120
ctctatgatg ctagctgaga tttttccaaa agaaaatggc ttaaataaaa ccctagagaa    6180
agaaaaactt taaatccctc caaagctcaa aagtaataga aacagatgag tttggagtca    6240
ggatttctct gtaagattgc ctaggctgtg tactgcacat ctccaggtgc cactgttgac    6300
agagattata actacaatgt gaagtgaatg gtgccactga cagttatgca aaccgtccag    6360
agcatagcca cctgatcctg ctgggattcc tcttgccagt ccatcagcag ttccccttga    6420
aagtttcacc aaacatccct taaatctgcc ctctcctgcc cgtccccagt ggaggtcctc    6480
atcatttttc acctgcattt ttgcaggagc tttcttatat ccaccttcct ccttttctct    6540
cagcccatca tctagctaca cagtctccag ggtaagcttt cagaaaggca atctcttgtc    6600
tgtaaaacct aagcaggacc aaggccaagt ttcttagcct gaaaaatgtg cttttctgac    6660
tgaactgttc aggcactgac tctacatata attatgcttt tctaccccct cacactcaac    6720
actttgactc cagcaatccc aaatccccag atccctaagt gtgctgtgct attttcacgt    6780
ggctctcaga cttggccagt gctgtttcca ttttggtctt tattccccac atctctgcct    6840
gggggtaga ttctaccctg aaaaatgttc ttggcacagc cttgcaaact cctcctccac     6900
tcagcctctg cctggatgcc cttgattgtt ccatgtcctc agcataccat gtttgtcttt    6960
cccagcactg acctaccatg tgtcacccct gcttggctgt accttccatg aggctaggac    7020
tatgtgtctc ctttgttgac tgctgttgcc ctagcatctt gcacagttcc ttgcacacaa    7080
```

```
ttagagctct ataaatgtca aataaatgtg ttataattat atgtttaaga tagttgttca     7140
aataaactct aaataacccc aac                                             7163

<210> SEQ ID NO 2
<211> LENGTH: 210
<212> TYPE: PRT
<213> ORGANISM: Homo sapiens

<400> SEQUENCE: 2

Met Trp Thr Leu Gly Arg Arg Ala Val Ala Gly Leu Leu Ala Ser Pro
1               5                   10                  15

Ser Pro Ala Gln Ala Gln Thr Leu Thr Arg Val Pro Arg Pro Ala Glu
            20                  25                  30

Leu Ala Pro Leu Cys Gly Arg Arg Gly Leu Arg Thr Asp Ile Asp Ala
        35                  40                  45

Thr Cys Thr Pro Arg Arg Ala Ser Ser Asn Gln Arg Gly Leu Asn Gln
    50                  55                  60

Ile Trp Asn Val Lys Lys Gln Ser Val Tyr Leu Met Asn Leu Arg Lys
65                  70                  75                  80

Ser Gly Thr Leu Gly His Pro Gly Ser Leu Asp Glu Thr Thr Tyr Glu
                85                  90                  95

Arg Leu Ala Glu Glu Thr Leu Asp Ser Leu Ala Glu Phe Phe Glu Asp
            100                 105                 110

Leu Ala Asp Lys Pro Tyr Thr Phe Glu Asp Tyr Asp Val Ser Phe Gly
        115                 120                 125

Ser Gly Val Leu Thr Val Lys Leu Gly Gly Asp Leu Gly Thr Tyr Val
    130                 135                 140

Ile Asn Lys Gln Thr Pro Asn Lys Gln Ile Trp Leu Ser Ser Pro Ser
145                 150                 155                 160

Ser Gly Pro Lys Arg Tyr Asp Trp Thr Gly Lys Asn Trp Val Tyr Ser
                165                 170                 175

His Asp Gly Val Ser Leu His Glu Leu Leu Ala Ala Glu Leu Thr Lys
            180                 185                 190

Ala Leu Lys Thr Lys Leu Asp Leu Ser Ser Leu Ala Tyr Ser Gly Lys
        195                 200                 205

Asp Ala
    210
```